US006692696B1

(12) United States Patent
Alberte

(10) Patent No.: US 6,692,696 B1
(45) Date of Patent: Feb. 17, 2004

(54) BIOSENSOR

(75) Inventor: Randall S. Alberte, Falls Church, VA (US)

(73) Assignee: Areté Associates, Sherman Oaks, CA (US)

(*) Notice: Subject to any disclaimer, the term of this patent is extended or adjusted under 35 U.S.C. 154(b) by 0 days.

(21) Appl. No.: 09/100,526

(22) Filed: Jun. 18, 1998

(51) Int. Cl.[7] .............................................. G01N 25/20
(52) U.S. Cl. .................. 422/50; 422/67; 422/68.1; 422/82.05; 422/52; 422/82.08; 422/83; 422/55; 435/252.3; 435/254.11; 435/257.2; 435/410; 435/817; 435/7.31; 435/4; 435/7.23; 435/6; 435/70.1; 435/325; 435/7.2; 435/7.21; 435/7.8; 435/7.1; 435/29; 435/34; 435/510; 436/501; 204/192.13; 204/403
(58) Field of Search ................... 422/50, 68.1, 82.05, 422/82.08, 83, 67, 55, 82.01, 52, 684, 63; 435/252.3, 254.11, 257.2, 410, 817, 7.31, 4, 254.21, 325, 7.21, 7.1, 7.2, 510, 288.7, 7.23, 6, 70.1, 7.8, 29, 34, 35; 364/497; 436/501; 536/23.1, 350; 438/909, 5; 204/192.13, 403.02, 400; 250/458.1, 288, 343, 252.1, 339.13, 361 C; 73/1.03, 1.06, 864.81

(56) References Cited

U.S. PATENT DOCUMENTS

| | | | | |
|---|---|---|---|---|
| 4,148,689 A | * | 4/1979 | Hino et al. ................... 195/65 |
| 4,347,320 A | * | 8/1982 | Borglum ..................... 435/144 |
| 4,859,609 A | * | 8/1989 | Dull et al. ................... 436/501 |
| 4,930,488 A | * | 6/1990 | Pearman et al. ............... 126/39 |
| 5,001,048 A | * | 3/1991 | Taylor et al. .................. 435/4 |
| 5,436,161 A | * | 7/1995 | Bergstrom et al. .......... 435/291 |
| 5,508,384 A | * | 4/1996 | Murphy et al. ............. 530/324 |
| 5,541,851 A | * | 7/1996 | Sato et al. ................... 364/497 |
| 5,576,210 A | * | 11/1996 | Sledziewski et al. .. 435/254.21 |
| 5,589,351 A | * | 12/1996 | Harootunian ................. 435/29 |
| 5,611,900 A | * | 3/1997 | Worden et al. ............. 204/403 |
| 5,756,351 A | * | 5/1998 | Isacoff et al. ............... 435/325 |
| 5,756,355 A | * | 5/1998 | Lang et al. ................. 435/7.21 |
| 5,866,430 A | * | 2/1999 | Grow .......................... 436/172 |
| 5,882,944 A | | 3/1999 | Sadee ......................... 436/501 |
| 5,891,646 A | | 4/1999 | Barak et al. ................. 435/7.2 |
| 5,958,703 A | * | 9/1999 | Dower et al. ................ 435/7.1 |
| 6,004,808 A | * | 12/1999 | Negulescu et al. ......... 435/325 |
| 6,096,509 A | * | 8/2000 | Okun et al. ................... 435/29 |
| 6,100,042 A | * | 8/2000 | Fowlkes et al. ............. 435/7.1 |
| 6,103,199 A | * | 8/2000 | Bjornson et al. ........... 422/100 |
| 6,103,537 A | * | 8/2000 | Ullman et al. .............. 436/526 |
| 6,110,693 A | * | 8/2000 | Barak et al. ................. 435/7.2 |
| 6,206,914 B1 | * | 3/2001 | Soykan et al. ............. 623/1.42 |
| 6,214,293 B1 | * | 4/2001 | Pantoliano et al. ........... 422/67 |
| 6,251,688 B1 | * | 6/2001 | Erb et al. .................... 436/518 |
| 6,495,102 B1 | * | 12/2002 | Suslick et al. ................ 422/55 |

FOREIGN PATENT DOCUMENTS

WO 97/35985 * 10/1997 ........... C12N/15/31

OTHER PUBLICATIONS

Barak, L.S. et al., A beta–Arrestin/Green Fluorescent Protein Biosensor for Detecting G Protein–coupled Receptor Activation. The Journal of Biological Chemistry. Oct. 31, 1997, vol. 272, No. 44, pp. 27497–27500.

* cited by examiner

Primary Examiner—Lynette R. F. Smith
Assistant Examiner—Ginny Allen Portner
(74) Attorney, Agent, or Firm—Peter I. Lippman

(57) ABSTRACT

Apparatus comprising G-protein coupled receptor (GPCR) for detecting ligands or substances in liquid or vapor media. The GPCR is based on in a cell or in a synthetic membrane or polymer system, and combined with means for obtaining a sample of a liquid or vapor medium, and with automatic optical detection system and monitoring system for detecting a ligand of interest. Methods are disclosed for detecting a ligand of interest using the GPCR apparatus.

38 Claims, 10 Drawing Sheets

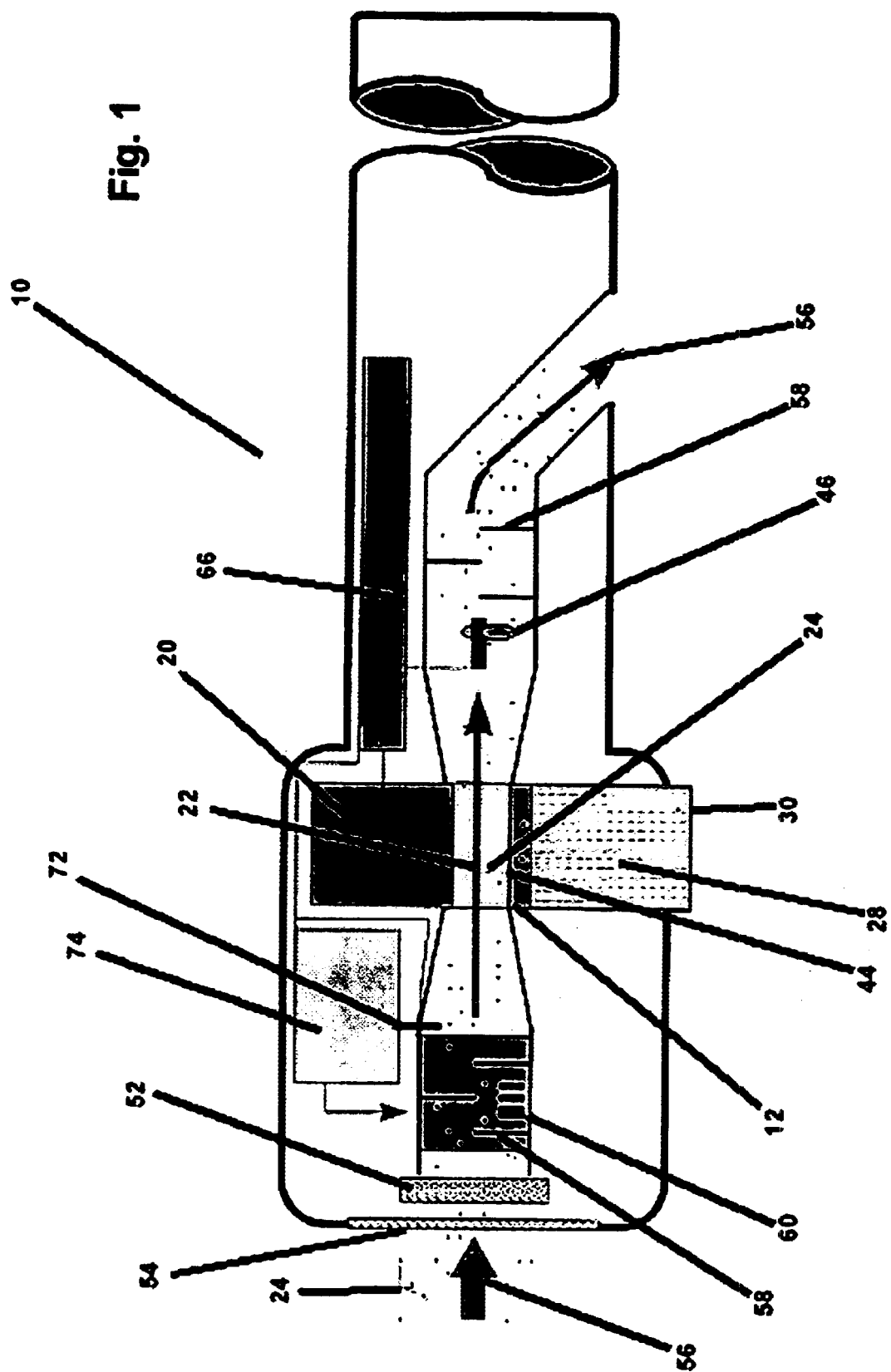

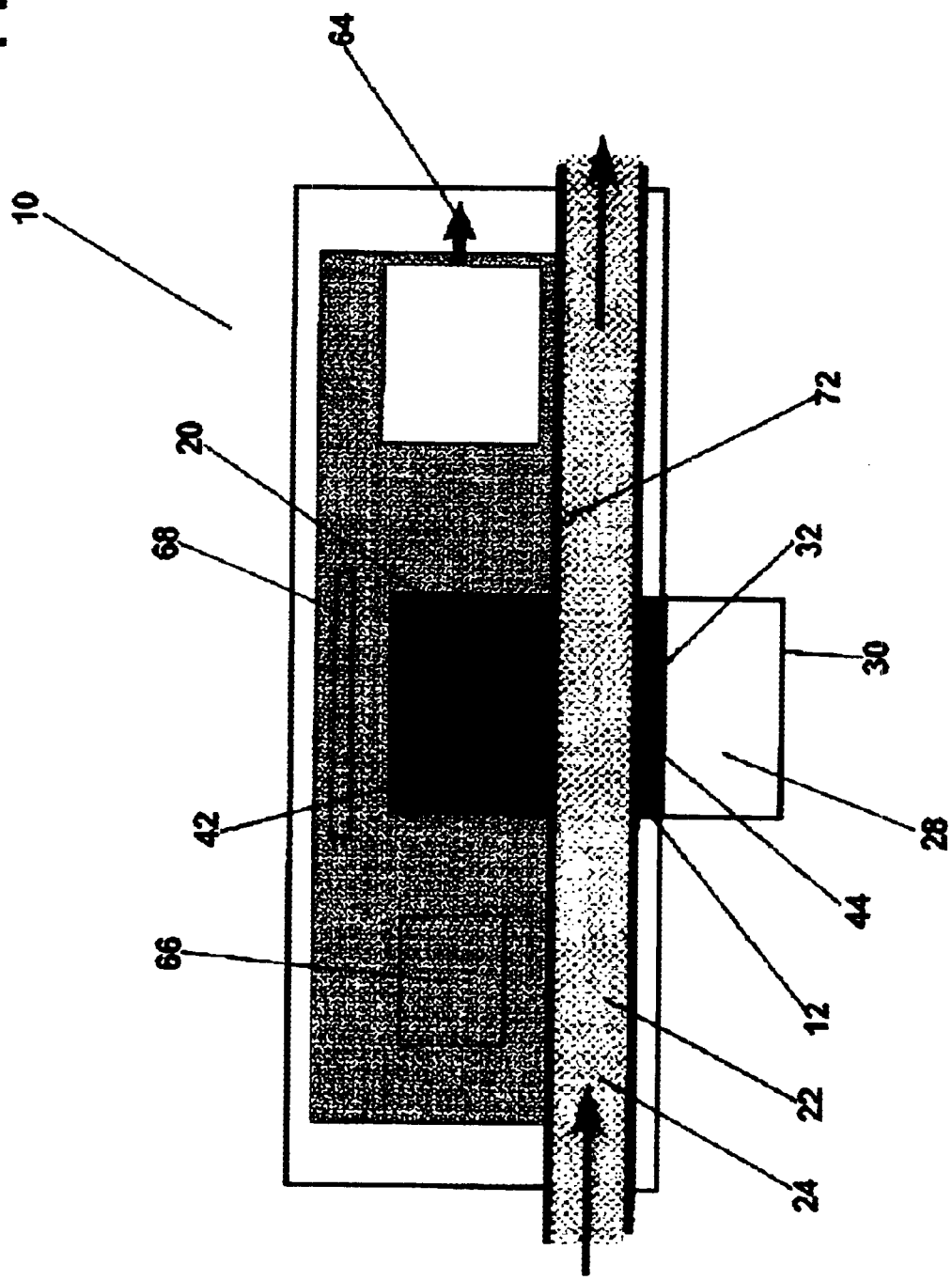

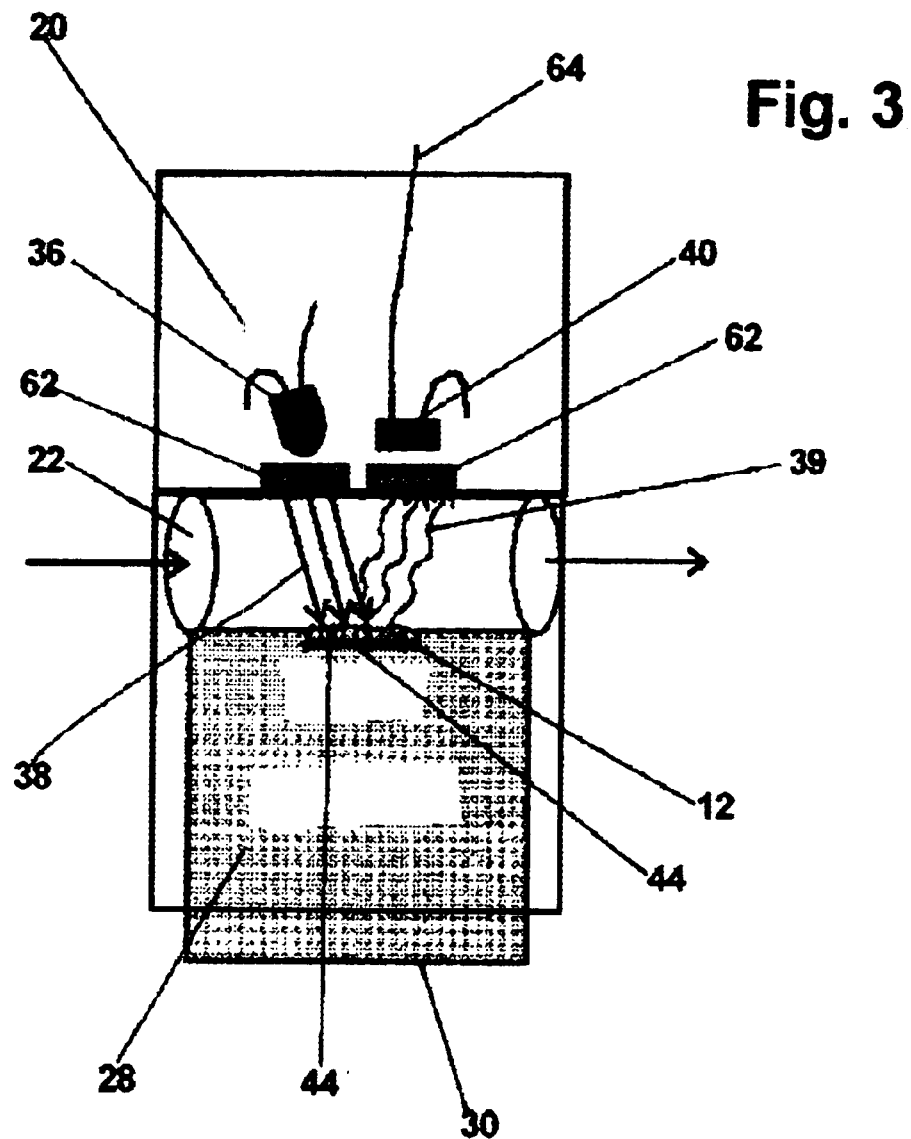

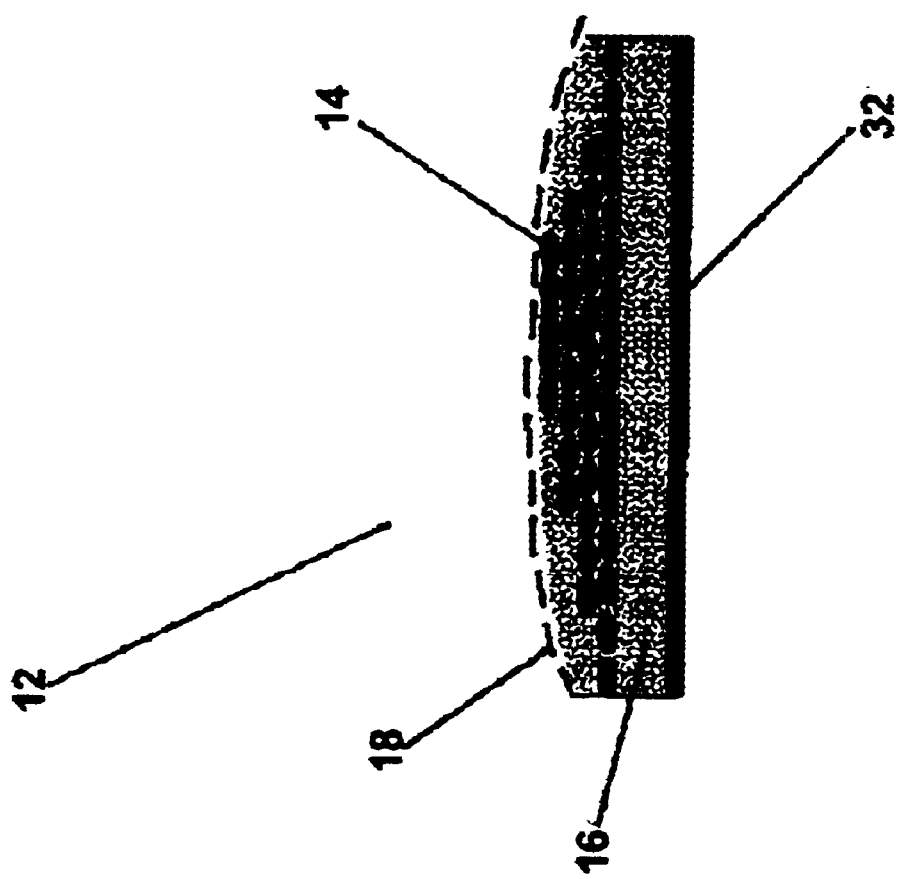

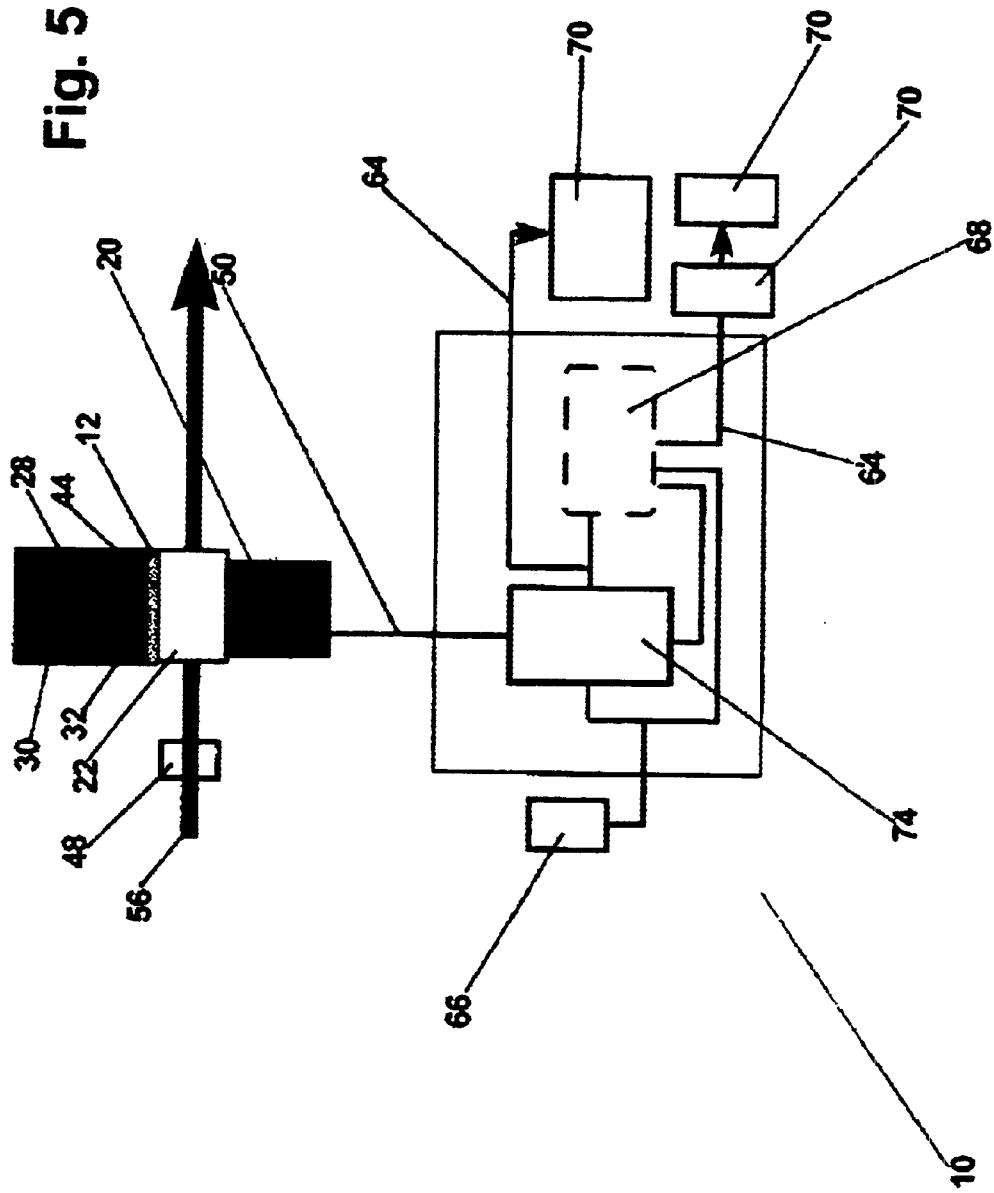

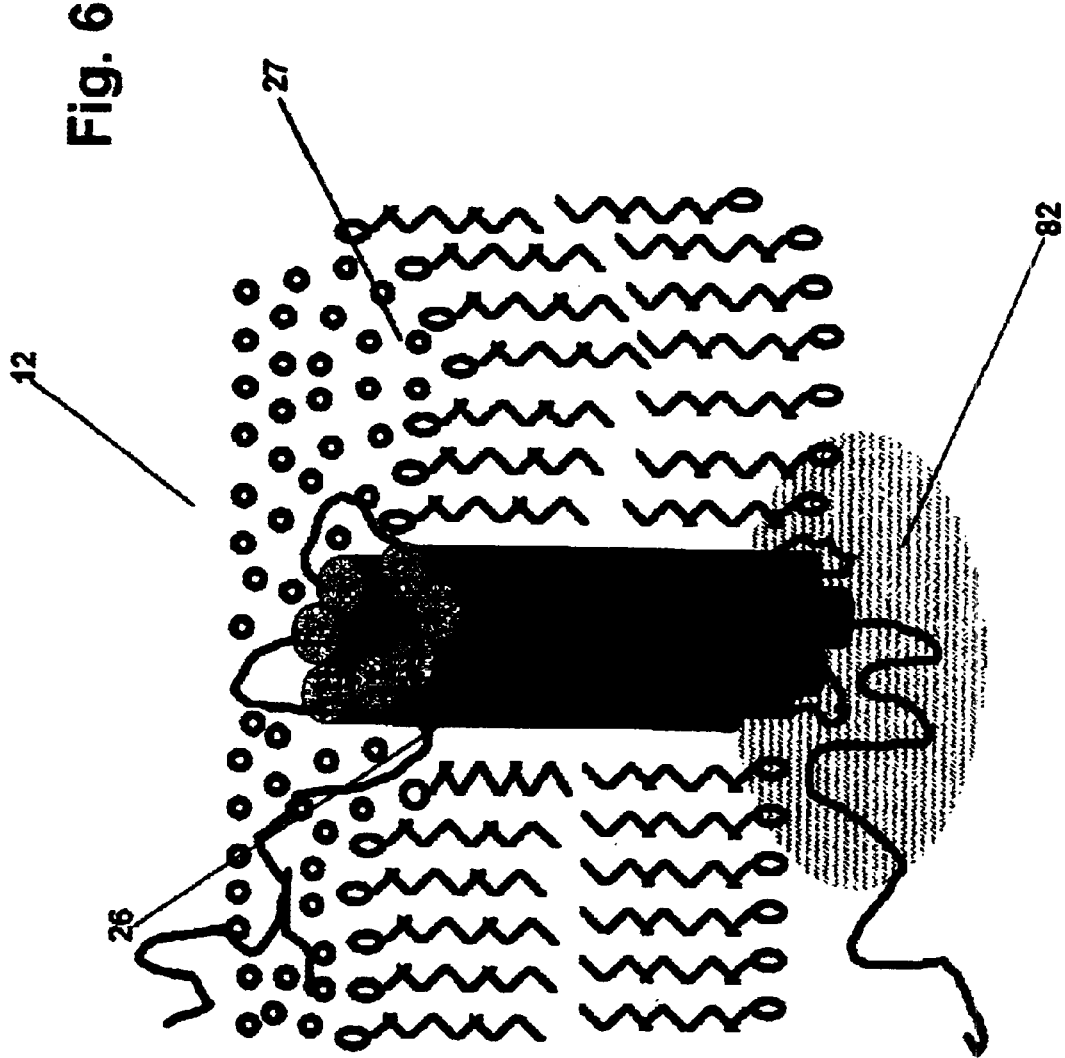

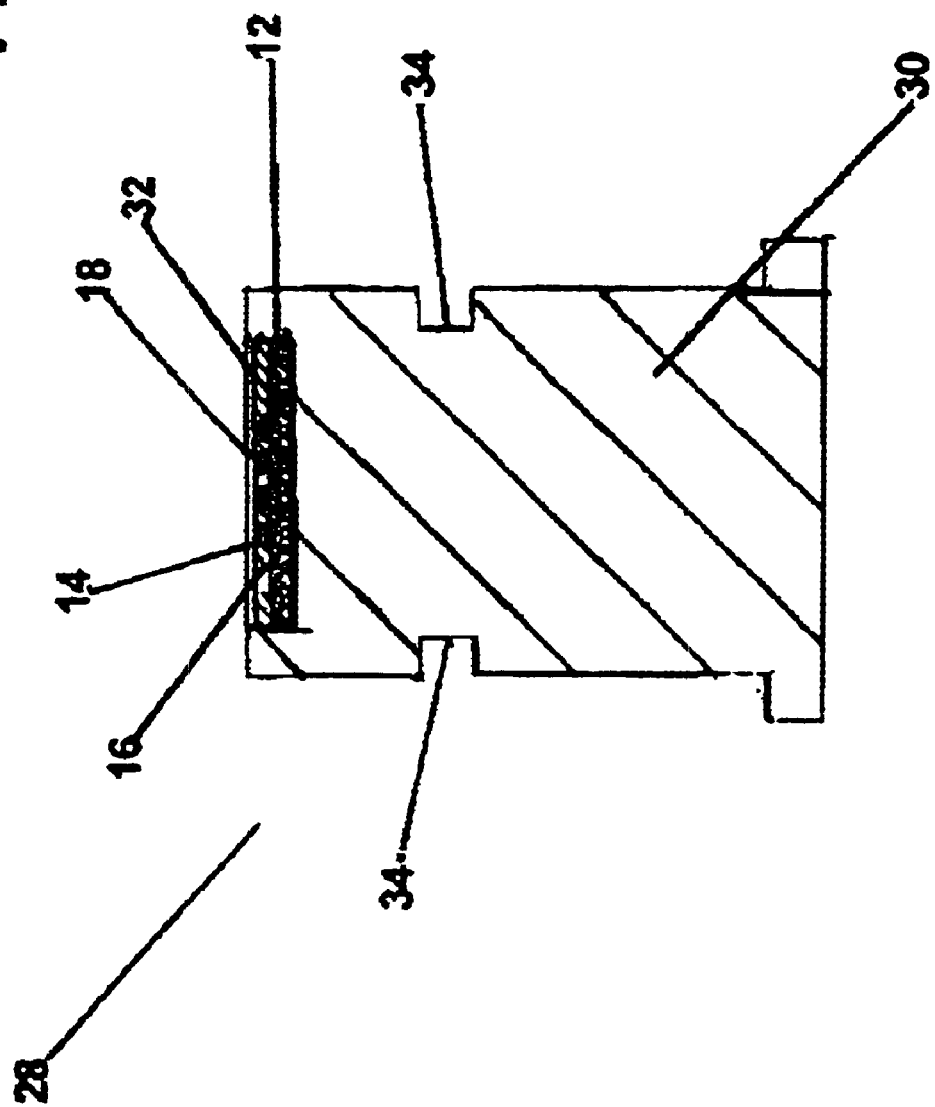

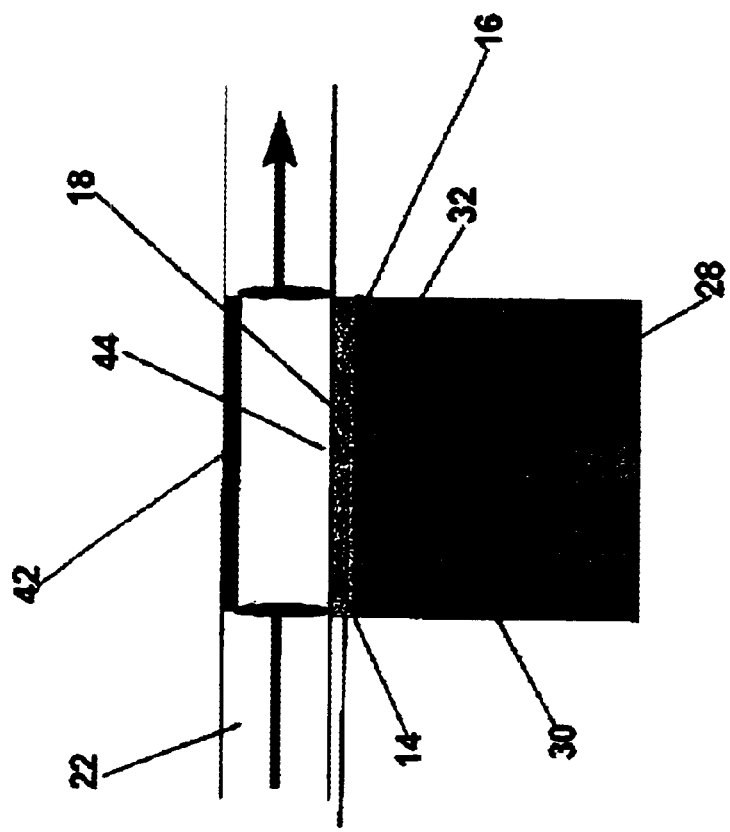

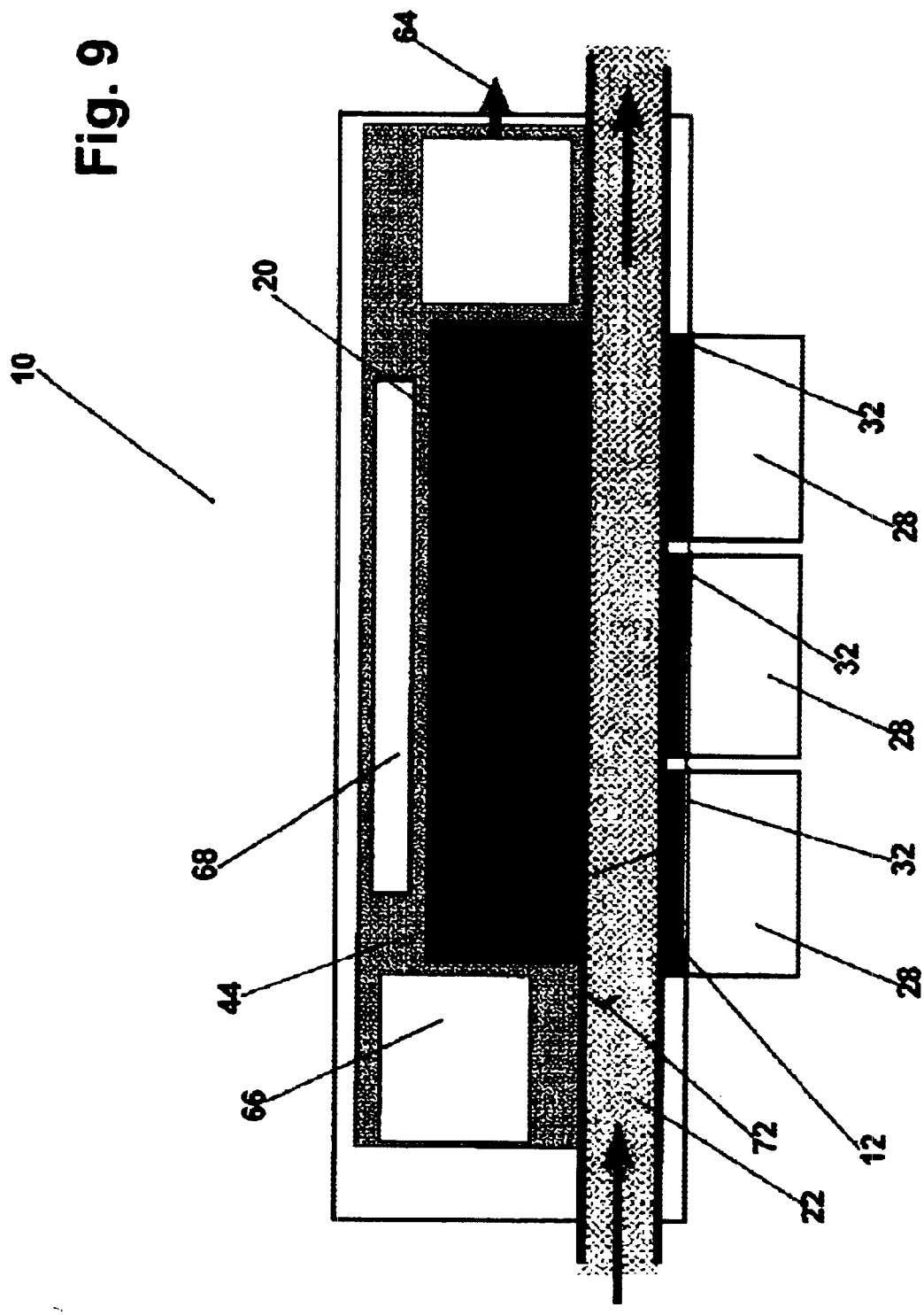

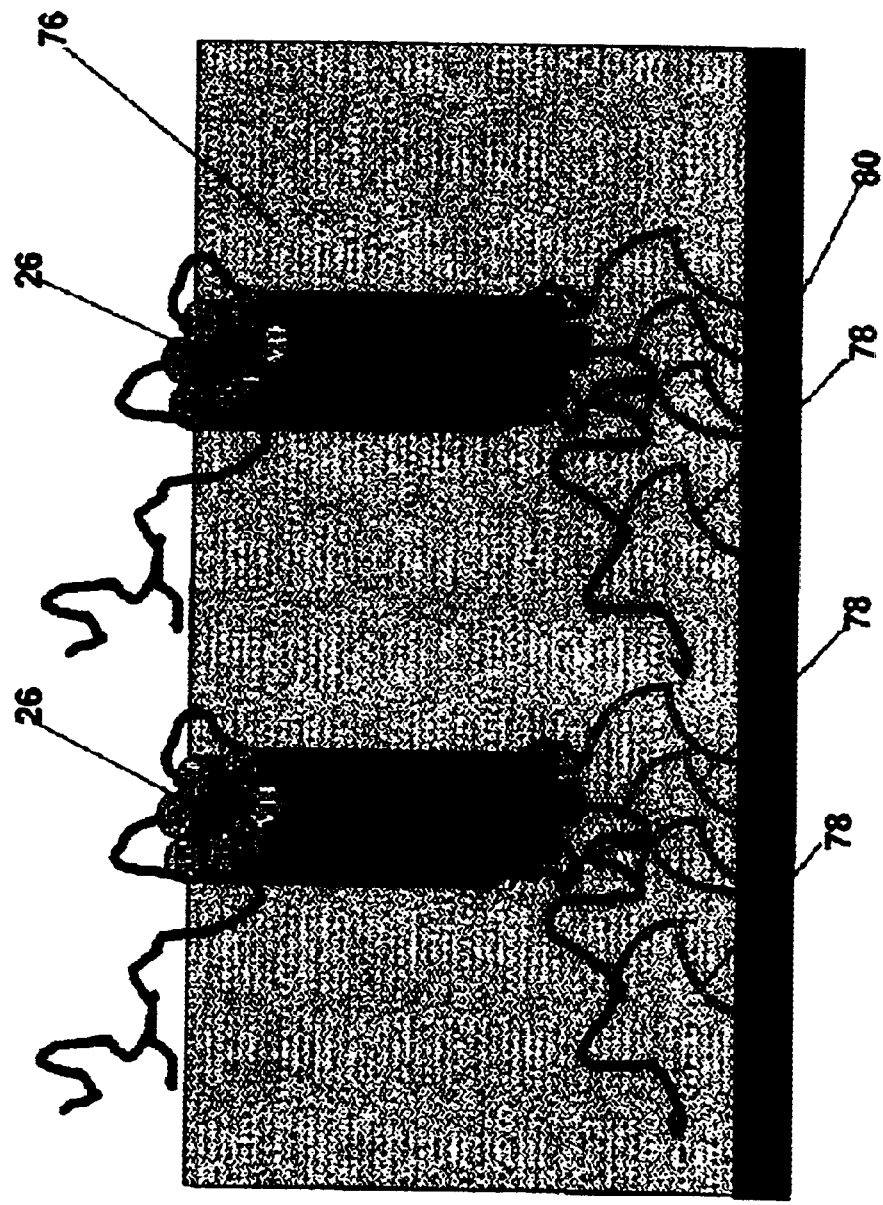

BIOSENSOR

BACKGROUND OF THE INVENTION

1. Field of the Invention

The present invention relates to methods and apparatus for detecting one or more ligands in candidate substances. More specifically, the invention is directed to methods and apparatus using biosensors incorporating G-Protein Coupled Receptors (GPCRs) for detecting specific substances or ligands, or for detecting specific objects or people associated with specific substances or ligands.

2. Description of Related Art

Biosensors have been in use for more than 30 years. In the past 7 to 8 years, however, the rate of development of biosensor technology has rapidly increased.

Biosensors are composed of a biological sensing element in intimate contact with some form of a physical transducer. Together, these two elements relate the concentration of a target analyte or ligand with some measurable signal. The earliest biosensors were simply enzymes immobilized on solid surfaces of oxygen electrodes which measured the consumption of oxygen in response to the enzymatic breakdown of substrate.

Enzyme-based biosensors have found their greatest use in the medical field for body fluid analyses (e.g. urine sugar content, blood sugar levels, serum cholesterol, lactate, and acetylcholine). Recently, a variety of other oxidative and reductive enzymes have been immobilized and coupled to colorimetric changes in product or to potentiometric or electrochemical changes in response to enzyme activities. These enzyme-based systems have been used most extensively for environmental monitoring (contaminants, pesticides, herbicides, and organic solvents) and in some cases for process stream monitoring. The sensors are suitable for multiple use and continuous monitoring up to certain limits. In general, end-product build-up leads to inhibition of the enzymatic activity, enzyme inactivation can occur as well as enzyme degradation all of which can lead to deterioration of the sensor function. Typical sensor lifetimes are only a few days.

Two additional types of biosensors have been recently developed and field-evaluated. One type exploits the highly selective recognition between antibodies and their antigens, while the second type exploits whole bacterial cells that report the presence of the target ligand through the production of light, or through a change in metabolic function.

An antibody sensor in an advanced state of development is that developed by the Naval Research Laboratory by Ligler (Naval Research Reviews, vol. 14, 1994). These biosensors use either monoclonal antibodies, which recognize a single epitope or site on the antigen or polyclonal antibodies, which recognize many epitopes on the antigen. The NRL biosensor can exploit two different types of immunological assay conditions. The response times for antibody sensors are in the range of minutes and sensitivities are nanograms per liter.

In one case, a sandwich immunological assay is used. In this assay type, antibodies for the target analyte or ligand are immobilized on an optical fiber. A solution containing the same antibodies which are labeled with a fluorophore is added with the experimental sample of ligand. The ligand binds to both sets of antibodies creating links between the immobilized antibodies on the fiber and the labeled antibodies. Thus the antigen is 'sandwiched' between the immobilized antibodies on the fiber and the labeled antibodies. The excitation of the fluorophore occurs through the fiber and only those fluorophores in very close proximity (ca. 150 nm) to the fiber (those bound in the sandwich) create an optical field on the surface of the fiber called the evanescent wave. This is the signal that is measured and it is proportional to the amount of ligand (and, consequently, fluorophore) bound to the fiber.

This type of antibody sensor requires sufficiently large antigens on the order of the size of small peptides (10,000 Daltons) to the size of large proteins (hundreds of thousands of Daltons), bacterial spores or viruses to ensure that a 'sandwich' is generated.

The second type of antibody sensor is based upon the competition between fluorescently labeled antigen and unlabeled antigen for binding sites on the fiber-immobilized antibodies. The same basic sensor design is used. The measurement is based on the reduction in fluorescence on the fiber due to binding of the unlabeled ligand which competes for sites where the labeled antigen was present in the initial calibration. The competitive immunoassay is highly suitable for small molecular species (e.g. less than 2000 Daltons). Other types of antibody sensors have been developed that exploit a variety of optical transduction schemes, including, resonance energy transfer between the chromophore bound on the antibody, which then transfers energy to chromophores bound to the ligand.

Cell-based sensors have also been developed. Among the most common to date, are genetically transformed bacterial cells are used in which the genes for bioluminescence (bacterial genes for bioluminescence are called lux genes) have been inserted to provide a means of reporting, through the generation of light, the presence of an analyte that is 'recognized' by the bacteria. For example, bacteria that possess the genes to bind intracellular copper ($Cu^{++}$) were transformed to possess the lux genes as well. When $Cu^{++}$ enters the cell, the genes encoding the copper-binding proteins are 'turned on' or expressed. Concomitant with the activation of the genes for $Cu^{++}$ binding is expression of the lux or light-producing genes. This coupling of gene expression for these two different functions is achieved by placing the lux genes under the influence of the promoter of the genes encoding the $Cu^{++}$ binding proteins. Consequently, when the cells take up $Cu^{++}$, they generate light thereby reporting the presence of intracellular $Cu^{++}$. The light emission can be detected with a CCD (Charged Coupled Device) camera, or if the cells are immobilized either on a fiber optic or a surface, the light production can be quantified using a CCD chip.

Since $Cu^{++}$ is the bioactive form of copper, the cell reports and can quantify the bioavailable copper in a sample making this biosensor more useful for many ecological and environmental studies than analytical techniques that quantify total copper. The current sensitivity of the copper biosensor is in the micromole range. In a similar fashion, investigators have linked lux genes to genes encoding degrading enzymes for a variety of organic toxicants such as naphalene and toluene and have achieved nano- to picomole sensitivities in cell-based sensors with high specificity.

Because these systems require gene expression in response to the presence of a target ligand to report the presence of the ligand, they do not possess rapid response times—generally 15–30 minutes for a detectable response and 60 minutes for maximal light production. However, they can be used remotely and can have significantly long operational lifetimes. More recently, bacterial metabolic functions have been exploited as biosensors. Intracellular degradation or conversion of target ligands are "reported" through the electrochemical detection of intermediates or end-products that are suitable for detection modes when the target ligand is not. Lastly, bacterial cell biosensors have been generated by the expression of non-endogenous enzymes on the cell surface that convert target ligands that are not normally taken up by the cells into chemical species that can be readily metabolized and reported as described above.

Tissue and organ based biosensors have also been developed. These often exploit insect antennae or excitatory tissues (neurons). Such biosensors are often coupled to electrical transduction and recording schemes. A major shortcoming to these technologies is the short (generally hours) operational lifetimes of the tissues or organs in the biosensor format.

The current technologies for ligand or substance detection in the vapor or aqueous phase of the environment and in medical or biological fluids of clinical subjects are generally costly, time-consuming and are, for the most part, not portable nor are they suitable for stand-alone, long-term surveillance or monitoring applications. There is a need for biologically based sensor technologies that offer an inexpensive solution to a broad range of ligand or substance detection (e.g. illicit drugs, explosives, environmental toxicants, process stream products or intermediates, chemical and biological warfare agents, and clinically important or relevant ligands) and provide long-term, stand-alone utility suitable for vapor- and/or liquid-phase detection modes.

DISCLOSURE OF THE INVENTION

The present invention, which is directed to methods and apparatus comprising GPCR-based biosensors for detecting ligands or substances, is intended to overcome the above-described limitations and deficiencies of currently available biosensors. The GPCR-receptor-based methods and apparatus for detecting specific substances achieve (a) more rapid turn-over times—in the millisecond time domain—than prior art biosensors, (b) greater ligand or substance range as many ligands of interest are too toxic for the generation of antibodies, other ligand species lack adequate antigenicity (e.g. metal ions, undecorated ring structures, certain small inorganic ion species, certain small organics), or many ligands of interest do not have a known or suitable enzymatic conversion process (due to unavailability of an enzyme, enzyme instability, or prohibitive cost of purification for a biosensor application). Accordingly, objects of the present invention include providing receptor-based biosensors that are less sensitive to interference to poisoning by other ligands which may be present under specific sensing conditions, have broad analyte detection capabilities, have highly selective ligand specificity, have receptors that are not consumed in the detection step and hence fully reversible, and have receptors that are stabilized for biosensor applications at low costs, and, in certain aspects, provide receptors in sensing elements that are highly tolerant of toxicants, including organic solvents.

The methods and apparatus provided by the present invention for detecting ligands or substances are advantageous due to their high sensitivity, rapid response time, high selectivity for single ligand or ligand class, high signal to noise ratio, self-calibrating capability, field portability and remote field applications, broad range of interrogatable systems (liquids, vapors), extended lifetimes of apparatus and stand alone use, cost-effectiveness and durability.

Vapor Phase or Liquid Phase Detection

In one aspect, the present invention is directed to a method for detecting a ligand in vapor phase. The method involves providing a sensing element which comprises a GPCR having preferential specificity for the ligand. The sensing element includes immobilized transformed eucaryotic cells heterologously expressing the GPCR, with the proviso that the eucaryotic cell line cannot be frog melanophore cells. In one aspect, the sensing element includes a fluorescing element that is selectively responsive to binding of the ligand to the GPCR. A preferred line of cells for use in the sensing element is a fungal cell line, in particular, a yeast cell line. A vapor phase or liquid phase specimen which contains a candidate substance is obtained, and the sensing element is exposed to the vapor- or liquid-phase specimen. The method further involves monitoring the response of the sensing element, and comparing the response with a previously established response for the ligand. A preferred form of monitoring comprises automatic optical detection of a change in optical characteristics of the sensing element.

The invention provides an apparatus for detecting a ligand in vapor- or liquid-phase. The apparatus comprises a sensing element which comprises a GPCR, means for exposing a candidate substance to the sensing element, and means for monitoring response of the sensing element. For example, a typical class of GPCRs which are adapted for use in the apparatus are Adrenoceptor GPCRs, mutants of which can be selected and incorporated into the apparatus or method of the invention for detecting explosives, like TNT because these GPCRs recognize small organics with aromatic rings.

The apparatus may comprise one or more different GPCRs. In one embodiment, the monitoring means comprises automatic optical means for detecting a change in optical characteristics of the sensing element. An embodiment of the apparatus' exposing means involves means for directing a vapor-phase specimen of the candidate substance to the sensing element. Another embodiment of the apparatus' exposing means involves means for directing a liquid-phase specimen of the candidate substance to the sensing element. The apparatus may further comprise means for comparing the response with a previously established response for the ligand and still further means for reporting that comparison electronically, optically or audibly. The apparatus may still further comprise utilization means which are responsive to the comparing means and for providing an appropriate action. The utilization means are selected from the group consisting of an annunciator for alerting an operator to results of the comparison; a door lock or other automatic access-control device for admitting or not admitting a person to a facility; a lock or other automatic access-control device for enabling or not enabling a person to have access to use of a facility, an apparatus, credit, information, a service or other data bases; and an automatic transport device for carrying or not carrying an object through or into a facility or apparatus.

Method and Apparatus for Detecting a Specific Substance

Another important aspect of the invention is directed to a method of detecting a specific substance which method involves the step of providing a GPCR that is specifically responsive to the specific substance. Suitable GPCRs are obtained from GPCRs well known in the art for their ligand specificity, or GPCRs are provided by conducting mutagenesis and selection on a known sequence of nucleotides encoding a GPCR, for example the sequence encoding Adrenoceptors GPCR or any other GPCR sequence, and selecting a sequence of nucleotides for a GPCR having preferential specificity for the specific substance. The GPCR (s), incorporated into a sensing element, are caused to be exposed to a candidate substance. In a preferred embodiment, transformed eucaryotic cells, in particular, yeast cells heterologously expressing a GPCR, are immobilized and incorporated into the sensing element. In one aspect, the sensing element further comprises a fluorescing element incorporated into the cells and which produces an response upon binding of a ligand of interest by the GPCR. The eucaryotic cells cannot be frog melanophore cells.

The GPCRs provided in the method of the invention are obtained by conducting mutagenesis and selection for GPCRs that are preferentially responsive to a specific substance. Examples of such substances include, but are not restricted to, an explosive and a narcotice or substances structurally or behaviorally related to an explosive or a narcotic. Examples of the explosive and narcotic include TNT and cocaine, respectively.

An apparatus is provided by the invention for detecting a specific substance. The apparatus comprises a GPCR, provided either from a GPCR of known specificity or derived by mutagenesis and selection and which is preferentially responsive to the specific substance. The GPCR is incorporated into a sensing element. The apparatus comprises means for exposing a candidate substance to the GPCR, and means for monitoring the response of the GPCR to the candidate substance. Embodiments of the apparatus comprises monitoring means for automatic detection of a change in optical characteristics of the sensing element. Still further embodiments of the apparatus include utilization means as described above.

Method and Apparatus for Detecting Specific Objects and People

In yet another aspect, the invention is directed to a method for detecting specific objects or people possessing, contaminated or otherwise associated with specific substances such as but not restricted to TNT or illicit drugs. The method involves exposing an object or person to a sensing element that includes a GPCR specific for the ligand of interest, monitoring the response of the GPCR, and comparing the response with a previously established response for a specific object or person. In the exposing step, the method includes exposing the object or person to a GPCR, and a preferred embodiment involves exposing the object or person to transformed eucaryotic cells heterologously expressing a GPCR, the cells being incorporated into the sensing element. Alternatively, the person or object is exposed to an array of GPCRs or an array of transformed eucaryotic cells with GPCRs having various sensitivities in the sensing element. With an array of GPCRs, the monitoring step is achieved by comparing a pattern of responses from the array with a previously established pattern of responses for a specific object or person. As above, the monitoring step includes automatic detection of a change in optical characteristics of the sensing element. Where the sensing element includes transformed eucaryotic cells, the monitoring step includes automatic detection of a change in optical properties (e.g., chromophore activated fluorescence) of the transformed cells.

The invention provides an apparatus for detecting specific objects or people, the apparatus comprising a sensing element that includes a GPCR, means for exposing an object or person to the sensing element, and automatic monitoring means connected to receive a response from the GPCR. A typical embodiment involves a transformed eucaryotic cells heterologously expressing a GPCR with specificity for the object or person with said substance which is incorporated into the sensing element. An embodiment of the apparatus includes utilization means.

Method and Apparatus for Detecting a Ligand

In yet another aspect, the invention provides a method for detecting a ligand, the method comprising the steps of exposing a candidate substance to a sensing element which includes a GPCR, monitoring response of the GPCR, and comparing the response with a previously established response for the ligand. An embodiment of the exposing step includes exposing the candidate substance to a sensing element which includes one or more different GPCRs. The method, which finds particular use in detecting a specific substance that includes the ligand, is directed alternatively to exposing a candidate substance to an array of the GPCRs having various different sensitivities, followed by a monitoring step which includes comparing a pattern of responses from the array with a previously established pattern of responses for the specific substance. As above, the GPCR can be derived from mutagenesis of a known sequence encoding a known GPCR and selection of a GPCR having a preferred specificity and sensitivity to the ligand or the specific substance that includes the ligand. The exposure step may involve obtaining a vapor or liquid phase specimen of the candidate substance and directing this specimen to the sensing element. The monitoring step can be either automatic optical detection of a change in optical characteristics of the sensing element, or automatic electronic detection of a change in electrical characteristics of the sensing element. Involvement of optical detection includes automatic optical detection of a conformationally amplified or induced change in fluorescence of the sensing element.

The apparatus for detecting a ligand comprises a sensing element which includes a GPCR, means for exposing a candidate substance to the sensing element, and means for monitoring response of the GPCR. As above, the sensing element may include one or more different GPCRs. In a typical embodiment, the GPCR is coupled with a chromophore and when responding to the ligand undergoes a conformationally induced change in fluorescence. The apparatus finds particular use in detecting a specific substance that includes the ligand, and the sensing element can include an array of GPCRs having various different sensitivities, and monitoring means that include means for comparing a pattern of responses from the array with a previously established pattern of responses for the specific substance. The GPCRs can be selected from GPCRs of known specificity or can be obtained by mutagenesis from a known or derived GPCR, and selection of GPCR fragments having the desired specificity and sensitivity to a ligand or specific substance of interest. Embodiments of the apparatus include monitoring means selected from the group consisting of automatic optical means for detecting a change in optical characteristics of the sensing element, and automatic electronic means for detecting a change in electrical characteristics of the sensing element.

A further embodiment of the apparatus includes means for directing a vapor- or liquid-phase specimen of a candidate substance to the sensing element. The apparatus further comprises means for comparing the response with a previously established response for the ligand. In yet another embodiment, the apparatus further comprises, as above, utilization means which are responsive to the comparing means, for providing an appropriate action. The utilization means are selected from the group consisting of an annunciator for alerting an operator to results of the comparison, a door lock or other automatic access-control device for admitting or not admitting a person to a facility, a lock or other automatic access-control device for enabling or not enabling a person to have access to use of a facility, an apparatus, credit, information, or a service, and an automatic transport device for carrying or not carrying an object through or into a facility or apparatus.

Method and Apparatus for Detecting Enumerated Substances

The present invention is further directed to a method of detecting specific substances including, but not limited to, chemical warfare agents, biological warfare agents, toxic agents, narcotics, pharmaceuticals, explosives, process stream analytes, impurities, waste materials, environmental pollutants, and clinically relevant ligands, typically, metabolites, hormones, electrolytes, nitric oxide, and proteins. The method comprises providing a coding sequence for a GPCR having a known specificity that is preferentially responsive to a specific substance selected from the group enumerated above. Another step of the method involves causing the GPCR, which is incorporated into a sensing element, to be exposed to a candidate substance. In preferred embodiments, the causing step includes at least one substep selected from the group consisting of incorporating the GPCR into a sensing element, shipping the GPCR to a person for use in screening for the specific substance, and providing instructions for use of the GPCR in screening for the specific substance.

The invention provides an apparatus for detecting any one of specific substances selected from the group consisting of chemical warfare agents, biological warfare agents, toxic agents, narcotics, pharmaceuticals, explosives, process stream analytes, impurities, waste materials, environmental pollutants, and clinically relevant ligands. The apparatus comprises a GPCR that is preferentially responsive to a specific substance selected from the group enumerated above. The apparatus also comprises means for exposing a candidate substance to the GPCR, and means for monitoring the response of the GPCR to the candidate substance.

Method and Apparatus to Detect Specific Substance Using GPCRs Situated in Eucaryotic Cells Synthetic Membranes or Polymer Systems In yet another aspect, the invention is directed to a method of detecting a specific substance, the method involving the step of providing a GPCR preferentially responsive to the specific substance. The GPCR is situated in a host structure selected from the group consisting of eucaryotic cells, a synthetic membrane system, and a synthetic polymer system. Another step of the method involves causing the host structure in which the GPCR is situated to be exposed to a candidate substance.

Accordingly, the invention provides apparatus for detecting a specific substance, the apparatus comprising a GPCR that is preferentially responsive to a specific substance and situated in a host structure selected from the group consisting of eucaryotic cells, a synthetic membrane system and a synthetic polymer system. The apparatus also comprises means for exposing a candidate substance to the host structure in which the GPCR is situated. The cell host structure of the apparatus is selected from the group consisting of eucaryotic cells. Typical synthetic membrane systems which find use in the invention are liposomes, other combinations of lipids, detergents, fatty acids and proteins that will form membrane-like vesicles. Typical synthetic polymer systems include but are not restricted to conducting organic polymers derived from aromatic or heteroaromatic materials e.g. polypyrrole, methyl pyrrole, poly(5-carboyindole).

Method to Detect Specific Substance Involving Manufacture of a Biosensor

Another aspect of the invention is directed to a method of detecting a specific substance which involves the step of manufacturing a biosensor that includes eucaryotic cells physically suspended on or in a hydrogel or other supporting material which serves to immobilize the cells and provide nourishment from material held within the hydrogel. Another step involves causing the cells to be exposed to a candidate substance.

A preferred embodiment of the method involves selecting transformed cells that heterologously express a GPCR which is preferentially responsive to the specific substance. The method further comprises the steps of monitoring response of the cells to the candidate substance, and the step of comparing the response with a previously established response for the specific substance. The monitoring step preferably includes automatic detection of a change in optical or electrical characteristics of the cells.

In another aspect, the method of detecting a specific substance involves the step of manufacturing a biosensor that includes one or more GPCR's having preferential ligand specificity and mounted in a synthetic polymer or synthetic membrane. The method further comprises the steps of monitoring response of the synthetic membrane or polymer to the candidate substance, and the step of comparing the response with a previously established response for the specific substance. The monitoring step preferably includes automatic detection of a change in optical or electrical characteristics of the synthetic membrane or polymer.

Method of Making a Biosensor for Detecting a Specific Substance and Apparatus Made Thereby A further aspect of the invention is directed to a method of making a biosensor for detecting a specific substance. The method comprises the steps of providing transformed cells which heterologously express a GPCR preferentially responsive to the specific substance; providing an immobilizing medium typically as a hydrogel; providing nourishment within the hydrogel for the cells; suspending the cells on or in the hydrogel to draw nourishment from material held within the hydrogel; and incorporating the hydrogel, with the cells and nourishment, into a carrier for exposure to a candidate substance. The cells for use in the method heterologously express a GPCR that is preferentially responsive to the specific substance. A further step involves functionally interconnecting the carrier with means for monitoring response of the GPCR to the candidate substance.

An apparatus made by this method is provided by the invention.

In another aspect, the method of making a biosensor for detecting a specific substance is directed the step of manufacturing a biosensor that includes one or more GPCR's having preferential ligand specificity and mounted in a synthetic polymer or synthetic membrane. The method further comprises the steps of monitoring response of the synthetic membrane or polymer to the candidate substance, and the step of comparing the response with a previously established response for the specific substance. The monitoring step preferably includes automatic detection of a change in optical or electrical characteristics of the synthetic membrane or polymer. An apparatus made by this method is provided by the invention

Apparatus for Detecting a Specific Substance

In particular, the invention provides an apparatus for detecting a specific substance, the apparatus comprising a sensor that includes a nourishing hydrogel serving to immobilize and nourish transformed eucaryotic cells that heterologously express a GPCR which is preferentially responsive to a specific substance. The apparatus also comprises means, responsive to a characteristic of the cells, for deriving a signal related to presence or absence of the specific substance. Also provided are means for exposing a candidate substance to the sensor. As above, a preferred embodiment of the cells are transformed cells which heterologously express a GPCR which is preferentially responsive to the specific substance. The signal-deriving means typically comprises means for monitoring the response of the GPCR to the candidate substance. The monitoring means typically includes means for automatic detection of a change in optical or electrical characteristics of the cells.

A preferred embodiment of the apparatus in which the signal-deriving means comprise means for monitoring the response of the GPCR to the candidate substances involves a further combination with automatic means for comparing the change in characteristics with a change in the same characteristics in presence of the specific substance. This further combination also involves utilization means, responsive to the automatic comparing means. The utilization means are selected from the group consisting of an annunciator for alerting an operator to results of automatic comparison, a door lock or other automatic access-control device for admitting or not admitting a person to a facility, a lock or other automatic access-control device for enabling or not enabling a person to have access to use of a facility, an apparatus, credit, information, or a service, and an automatic transport device for carrying or not carrying an object through or into a facility or apparatus.

Method of Detecting Specific Substance Involving Manufacturing a Biosensor

Yet another aspect of the invention is directed to a method of detecting a specific substance, the method comprising the step of manufacturing a biosensor that includes a GPCR which is preferentially responsive to the specific substance. The GPCR comprises or incorporates a signaling element selected from the group consisting of a chromophore for responding to a substance by fluorescing, and an electrical mechanism for responding to a substance by a change in an electrical property. The GPCR also has incorporated a conformational response for inducing the signaling, in comparison with a background signal level. The method also involves causing the biosensor to be exposed to a candidate substance. Further comprising steps of the method are monitoring response of the biosensor to the candidate substance, and the step of comparing the response with a previously established response for the specific substance. Preferably, the monitoring step includes automatic detection of a change in optical or electrical characteristics of the biosensor.

Method of Making a GPCR or Fragment Thereof for Use in a Biosensor To Detect a Specific Substance, and a GPCR or Fragment Thereof Made Thereby The invention in another aspect is directed to a method of making a GPCR for use in a biosensor to detect a specific substance. The method comprises the steps of providing a GPCR that has a preferential response to the specific substance. The method involves the step of incorporating into said GPCR a signaling element selected from the group consisting of a chromophore for responding to a substance by fluorescencing, and an electrical mechanism for responding to a substance by a change in an electrical property. Another step is directed to incorporating into said GPCR a conformational response for inducing the signaling, in comparison with a background signal level.

Another aspect of the invention is directed to a GPCR made by the above method.

Apparatus for Detecting a Specific Substance

The invention is further directed to an apparatus for detecting a specific substance, in which the apparatus comprises a biosensor that includes a GPCR preferentially responsive to the specific substance and which incorporates a signaling element selected from the group consisting of a chromophore for responding to a substance by fluorescing, and an electrical mechanism for responding to a substance by a change in an electrical property. Also, the GPCR incorporates a conformational response for inducing the signaling, in comparison with a background signal level. The apparatus also includes means for exposing the biosensor to a candidate substance.

In another aspect, the invention is directed to an apparatus for detecting a specific substance, the apparatus comprising at least one biosensor that includes a GPCR which is preferentially responsive to the specific substance. The apparatus also comprises means for exposing the biosensor to a candidate substance, means for monitoring the GPCR response, and at least one independent, demountable cartridge for holding the biosensor and for use by an operator in selectively disposing the biosensor in position relative to the exposing means and the monitoring means for detection, or removing the biosensor from position for detection. In one embodiment, the biosensor of the apparatus includes a host structure which encompasses the GPCR, and the cartridge also includes resources for maintaining the host structure, with the GPCR in operable condition. A typical host structure includes transformed eucaryotic cell which heterologously express GPCR, the cells deriving nutrition from resources included in the cartridge that comprise nutriments for sustenance of the cells. A version of the apparatus is directed to one in which the cartridge is for disposal or replenishment when the nutriments are exhausted or the cell viability has declined. Another embodiment of the apparatus further comprises a multiplicity of GPCRs representing different types, respectively, preferentially responsive to a corresponding multiplicity of respective different specific substances. In this embodiment, there is a corresponding multiplicity of cartridges, respectively holding different ones of the GPCRs, the cartridges being substantially interchangeable. Accordingly, with a multiplicity of GPCRs and the correspondingly multiplicity of cartridges, the apparatus is efficiently usable by an operator for detecting selectively any of the multiplicity of specific substances.

The above-discussed and many other features and attendant advantages of the present invention will become better understood by reference to the following detailed description of the invention taken in conjunction with the accompanying drawings.

BRIEF DESCRIPTION OF THE DRAWING

FIG. 1 shows an embodiment of the apparatus for vapor phase detection of a ligand.

FIG. 2 shows an embodiment of the apparatus for liquid phase detection

FIG. 3 shows a sensing element in the form of a cartridge and optical detection elements.

FIG. 4 shows a sensing element with cells immobilized on hydrogel.

FIG. 5 is a schematic diagram of an embodiment of the apparatus of the invention showing the electrical and electronic elements for automatic optical detection, monitoring, and data output as functionally connected to the sensing element in the form of a cartridge mounted on a flow chamber.

FIG. 6 shows a schematic diagram of a typical GPCR in a cell membrane revealing analyte recognition domains and G-protein coupling domains.

FIG. 7 shows a demountable i.e replaceable cartridge.

FIG. 8 shows a demountable cartridge with an optical window for mounting adjacent to the optical detection system.

FIG. 9 shows an embodiment of the apparatus having a plurality of demountable cartridges.

FIG. 10 shows an oriented GPCR embedded in a synthetic membrane or polymer system.

MODES OF CARRYING OUT OF THE INVENTION

General Description and Definitions

The practice of the present invention will employ, unless otherwise indicated, conventional biochemistry, molecular biology and recombinant DNA techniques within the skill of the art. Such techniques are explained fully in the literature. See, e.g. Maniatis et al., *Molecular Cloning: A Laboratory Manual* (1982); *DNA Cloning: A Practical Approach*, vol. I & II (D. Glover, ed.); Oligonucleotide Synthesis (Gait, N., ed., 1984); *Nucleic Acid Hybridization*, B. Hames & S. Higgins, eds., (1985); Sambrook, J. et al. vol. 1–3, Molecular Cloning, A Laboratory Manual, 1989; Harwood, A.J., ed. (1996) Basic DNA and RNA Protocols, Humana Press, NJ; Glover, D. M. and Hames, B. D. (1995) DNA Cloning: A Practical Approach, 2nd ed. vol. 1–4, IRL Press; Kriegler, M. (1990) Gene Transfer and Expression, A Laboratory Manual, Stockton Press, NY.

Further reference is made to standard techniques, materials, and equipment in biosensors, and electronics for detecting, monitoring, and processing optical or electrical characteristic changes of sensing elements. Factors, techniques, and equipment involved in biosensor construction, performance and application of biosensors to health care, control of industrial processes, environmental monitoring are explained fully in the literature. The electroanalytical methods of potentiometry, voltammetry and conductivity, as well as optico-analytical transducers and device construction are disclosed and explained in standard references. Also available in the literature are methods for optimizing performance factors: selectivity, linear range, calibration, reproducibility, response time, lifetime and the factors affecting biosensor performance (e.g. pH, buffers, methods and materials for immobilizing living cells. See, e.g., Janata, J., *Principles of Chemical Sensors*, (1989), Plenum Press; Eggins, B. R., *Biosensors—An Introduction*, (1996), John Wiley & Sons Ltd.; Kress-Rogers, E., ed., *Handbook of Biosensors and Electronic Noses*, Medicine, Food and the Environment (1997), CRC Press; Fraser, D. M., *Biosensors in the Body: continuous in vivo monitoring*, (1997), John Wiley & Sons; Bickerstaff, G. F. ed., (1997) Immobilization of Enzymes and Cells, Humana Press, Inc., Totowa, N.J.

The following terminology will be used in accordance with the definitions set out below in describing the present invention.

As used herein, the term 'biosensor' refers to the apparatus of the invention which comprises an analytical device that incorporates a biologically active material in intimate contact with an appropriate transduction element for the purpose of detecting—reversibly and selectively—the concentration or activity of chemical species (ligands) sampled by the biosensor from the vapor phase or aqueous (liquid) phase. The term 'biosensor' also refers to a self-contained analytical device that responds selectively and reversibly to the concentration or activity of chemical species or ligands in biological samples. Accordingly, the apparatus of the present invention comprises a biosensor for practical applications in medicine, environmental protection, security, process monitoring, law enforcement, and process stream monitoring.

As used herein, the terms "substance" and "ligand" are used to describe chemicals as follows: In some contexts, substance is used to refer to a candidate material which might or might not contain a ligand that the methods and apparatus of the invention are detecting. In other words, ligand is the chemical entity the methods or apparatus is looking for, and substance is the material in which the methods or apparatus are looking for it. In other contexts, substance is used for both the ligand or specific material that the methods and apparatus are looking for and the material in which it is being looked for (but the two are distinguished from one another by the term candidate appearing in the phrase "candidate substance"). In still other contexts, substance is used to refer to a material that the methods and apparatus are looking for, and that is known to contain a particular ligand—and the ligand is the target that the methods and apparatus use to seek and detect that sought-after material. Another definition of the term "ligand" as used herein is a molecule capable of being bound by the ligand-binding domain of a receptor, namely a GPCR. The molecule may be chemically synthesized or may occur in nature.

As used herein, the term "contaminant" means any substance determined to be unacceptable to the system or medium, which substance could include toxicants (toxic agents) or other substances which are not toxic under normal environmental conditions, but due to their elevated concentrations can be hazards to human health or environmental stability.

As used herein, the term "eucaryotic cells" or "eucaryotes" refers to cells with nuclei, with the understanding that frog melanophore cells, which are eucaryotic, are not included.

A "G-Protein Coupled Receptor" (GPCR) is defined to be any cell surface transmembrane protein that when activated by the binding of a chemical ligand or specific substance, in turn activates a hetertrimeric guanine nucleotide-binding protein (G-protein). (Strader, C. D. et al. Ann Rev. Biochem (1994)63:101–32). In living cells, GPCRs are localized within cell membranes and operate to communicate chemical signals (ligands or specific substances) from the extracellular environment to the inside of the cell. GPCRs are known in most eucaryotic cell types, and have been characterized in many vertebrate cell types (e.g fibroblasts, neuronal cells). GPCRs have also been well characterized in yeast. G-protein encoding sequences have also been found in algal and plant cells, though to date, their corresponding GPCR encoding sequences have yet to be sequenced. (Paine, K. et.al. (1993) J. Exp. Bot. 44:183–195; Faby, S. and Baer, K. (1996) Protoplasma 190:79–87; Ma, H. (1994) Plant Molec. Biol. 26:1611–1636; Milner, P. A. and Causier, B. E. (1996) J. Exp. Bot. 47:983–992; Faby, S. et al. (1995) Molec. Gen. Genet. 247:265–274).

The GPCR for the aromatic compound epinephrine has a domain exposed to the outside of the cell that provides some preferential recognition for this molecule. It is, however, the highly selective and specific binding of the epinephrine to specific sites in the transmembrane regions (typically the membrane-spanning regions identified as V and VII) that initiates signal transduction and the coupling of the receptor to the G-proteins that reside inside the cell in the cytoplasm (Strader, C. D. et al. Ann Rev. Biochem (1994)63:101–32; Dohlman, H. G. et al. (1991) Ann. Rev. Biochem. 60:653–688). At this step, recognition of the ligand is established. Generally, this is followed by the activation of adenylcyclase and the subsequent production of cyclic AMP (cAMP) which serves as a second messenger in the signal transduction scheme. In certain cells types e.g., vertebrate excititory cells—Bean, B. P. (1989) Ann. Rev. Physiol. 51:367–384; yeast cells—Prasad, K. R. and Rosoff, P. M. (1992) Cell Calcium 13:615–626), concomitant with the binding of the analyte is a flux of $Ca^{++}$ from the extracellular medium to the inside of the cell leading to a transient increase in the free $Ca^{++}$ levels in the cytoplasm (Neer, B. J. (1995) Cell 80:249–257). A unique feature of the present invention is based upon the concomitant influx of $Ca^{++}$ from the extracellular milieu into the cell upon GPCR-ligand binding which makes it possible to exploit the rapid (e.g., milliseconds) $Ca^{++}$ flux when coupled to a vital flourescent dye that binds free $Ca^{++}$ for optical detection of the rapid fluorescence response to detect a ligand.

A GPCR is considered to be useful in those aspects of the present invention which employ cell-based sensors. In particular, the cells are transformed and heterologously express a GPCR that is coupled to an endogenous calcium channel. The term "heterologous expression" means transcription and translation of nucleotide sequences which are not native to the cell but which have been incorporated into the cell's chromosomal or extra-chromosomal expression system genetic engineering techniques known in the art. The cells contain a $Ca^{++}$ binding chromophore or fluorophore and the GPCR is capable of specifically binding a ligand of interest. Binding of the ligand of interest to the GPCR causes, among other signals, a $Ca^{++}$ influx, which elicits a cellular response—chromophore activated fluorescence—which can be monitored to detect the ligand of interest, and in preferred aspects, compared with a previously established response for the ligand and in other aspects, coupled with utilization means for providing appropriate actions as described in detail below.

G-protein coupled receptors are capable of detecting thousands of natural and synthetic molecular species ranging from metal ions like calcium to sugars (sucrose and fructose), small aromatic molecules (e.g. epinephrine, catecholarnines and molecular species of less than 1,000 daltons), peptides and proteins (e.g. Nutrasweet™ to proteins up to 10 kilo daltons), and lipids. (Strosberg, A. D., Eur. J. Biochem. (1991) 196:1–10; Fraser, C. M., J. Nucl. Med (1995) 36:17–21; Watson, S. & Arkinstall, S., The *G-Protein Linked Receptor Facts Book*, (1994), Academic Press; Zhao, H. et al. (1998) Science 279:237–242). In principal, the range of chemical structures than can be detected by GPCRs suitably made by techniques for mutagenizing and selecting an initially known GPCR, which techniques are well known in the art, is unlimited.

It will be understood that as used herein, the term "GPCR" also refers to an active fragment of a GPCR. The active fragment of GPCR has the characteristic of possessing the ligand binding domain of the GPCR from which it was derived, thereby retaining ligand recognition/binding specificity. As explained below, for electrical monitoring of cell response, the fragment may lack the G-protein signaling portion, which would prevent the signal cascade and whole cell response to ligand detection or binding (e.g. calcium flux induced fluorescence). However, in no instances where the invention relies on chromophore activated fluorescence linked to $Ca^{++}$ influx will the fragment lack the G-protein signaling portion (Wess, J. FASEB J. (1997) 11:346–354). Furthermore, methods are known in the art for selecting GPCR fragments which retain both ligand binding specificity and G-protein signal transduction capability.

It will be understood that the term "sensing element which includes a GPCR" is used to include (1) a single GPCR specific for a single ligand; (2) a plurality or array of different GPCRs specific for a plurality of specific ligands, respectively; (3) a plurality or array of different GPCRs specific for a single ligand (particularly for a large molecular species of a ligand).

Mutagenesis and Selection of New GPCRs Preferentially Responsive to a Specific Ligand or Substance It is understood that new GPCRs with desired selective or specific binding to one or more target ligands or target materials are obtained by mutagenizing a nucleotide sequence encoding a GPCR to express variants in the GPCR, and selection of the desired variant(s). It should be emphasized that, as described below, techniques are well known for selecting, cloning, and expressing a GPCR encoding sequence (U.S. Pat. No. 5,691,188 and U.S. Pat. No. 5,482,835, hereby incorporated by reference; also see PCT International Publication No. WO 97/48820) which binds to one or more target materials, and/or fails to bind to one or more target materials.

Specificity is the ability of a binding molecule, in this case, a GPCR, to bind strongly to a limited set of target substances or materials, while binding more weakly or not at all to another set of target substances from which the first set must be distinguished. It should be understood that it is well known in the art that active fragments of a GPCR are obtainable that, despite not being a whole GPCR, exhibit a specificity that is either the same or different from the whole GPCR from which the fragment was obtained (Heyes et al. (1998) Biosensor 1998 (Abstr.), Turner, A. F. D. ed., p. 159, Elsevier Press). The ligand-binding specificity resides in the ligand-binding domain of the whole GPCR or fragments thereof that possess all or a portion of the transmembrane regions (Xie, G-X. et al. PNAS USA. (1992) 89:4124–4128; Strader, C. D.,.et al. Ann. Rev. Biochem. (1994) 63:101–132; Guan, X-M., et al. Molec. Pharmacol (1995) 48:492498).

To those skilled in the art, a large body of literature is available which teaches how (in the genetic sense) to generate, select, and structurally and functionally analyze GPCRs for ligand specificity. (U.S. Pat. Nos. 5,462,856; 5,385,831; 5,284,746, 5,576,210; 5,482,835; 5,607,836; 5,596,088; 5,691,188) (Fraser, C. M,. J. Nucl. Med. (1995) 36:17S; Strosberg, A. D., (1991) Eur. J. Biochem. 196:1–10; Spalding, T. A. et al. (1995) Pharmacol. Exptl. Therap. 275:1274–1279). Many technical approaches are available for using recombinant DNA technology in the design, selection, and expression cloning of GPCR sequences in a wide variety of eucaryotic cell systems (Xie, G.-X., et al. (1992) PNAS USA 89:4124–4128; Machida et al. (1988) Opiod Peptides: An Update; NIDA Resch Monograph 87, R. S. Rapaka et al., eds, Natl. Inst.on Drug Abuse; McClintock, T. S., et al. (1993) Analyt. Biochem. 209:298–305; Lerner, M. R. (1994) Trends Neurosci. 17:142–146; Medici, R. et al. (1997) EMBO J. 16:7241–7249).

The variant GPCRs are screened for the trait desired, that is, preferential binding of a particular ligand or specific substance. Binding of the ligand to GPCRs is coupled to an event that can be easily observed or evaluated.

Techniques well known in the art are available to selectively enhance mutation rates of very small regions of DNA. These regions code for only a single amino acid in the protein product, thus allowing single amino acid substitutions in the primary structure of proteins. In addition to random mutagenesis techniques, this process, known as site-directed mutagenesis, coupled with well known techniques to select variants of gene and protein structure provides a very powerful and rapid means to create and identify new protein products, and in particular, new GPCRs for use in the present invention that are preferentially responsive to a specific substance or ligand based on a highly selective and specific binding of the substance or ligand to the new GPCR. Any program of mutagenesis and selection of either a known, defined nucleotide sequence encoding a GPCR of known specificity or of an undefined nucleotide sequence encoding a GPCR finds use in the present invention for obtaining a GPCR that is preferentially responsive to a ligand of interest.

For example, if one takes a known GPCR and subjects the gene to random mutagenesis (Oliphant, A. R. and Struhe, K. (1989) PNAS 86:9094–9098; Yaghaniai, R. and Hazelbauer, G. L. (1992) PNAS 89: 7890–7894; Bowie, J. U. and Sauer, R. S. (1989) PNAS 86:2152–2156), many ($10^{6-8}$) new variants in the receptor can be generated in the laboratory. The variants can be rapidly screened for the trait desired, e.g. binding of cocaine or heroin, using a cell expression system where the variant receptors are expressed in a cell line where they can be coupled to an event that can be easily observed or evaluated (induced fluorescence of a calcium binding fluorophore by calcium influx activated by the GPCR binding a ligand of interest, which is explained in detail below). Variants of choice are then subjected to further rounds of mutation and selection until variants are obtained that possess the desired trait. This approach to the generation of novel proteins or proteins with new or modified functions (e.g, substrate specificity) has been referred to as "irrational mutagensis" by Arnold (Shao, Z. & Arnold, F. H., Curr. Opinions in Struct. Biol. (1996) 6:513–518). Other approaches to generating variant GPCRs are based on site-directed mutagenesis ("rational" mutagenesis) using methods well known in the art. In a further example, given a suitable biomolecular receptor or channel framework, encoded combinatorial synthesis (Smith, M. (1985) Ann. Rev. Gen. 19:423–462; Krebs, J. F., et al. (1993) J. Biol. Chem. 268:948–954; Leung, D. W. et al. (1989) Technique-J. Meth. Cell. Mot. Biol. 1:11–15) can be used to generate the desired receptor variants for the array. The protocol involves (partial) randomization of the polypeptide sequence, display of the resulting sequence variants in a library, selection or screening in the library for the desired variants (e.g. by ligand binding criteria) and, finally, scaled up synthesis of the preferred receptor variants. Further elaborations on mutagenesis, selection, and cloning are found in Marks, J. D. et al. (1992) J. Biol. Chem. 267:16007–16010; and Parniley, S. F. (1988) Gene 73:305–318; Boussiont, A. N. et al. (1997) Anal. Biochem. 249:119–130; Blumer, K. J. and Thomer, J. (1991) Ann. Rev. Physiol. 53:37–57).

Scope of Lipands Detectable by the Method and Apparatus of the Invention

It should be understood that the scope of ligands or target materials of interest for which new GPCRs can be generated by recombinant DNA techniques described above is extremely large. Known GPCRs respond to a vast number and variety of ligands, which include but are not limited to metal ions, sugars, small aromatics, peptides, proteins, lipids, certain bacteria and viruses (Strosberg, A. D., Eur. J. Biochem. (1991) 196:1–10; Fraser, C. M., J. Nucl. Med (1995) 36:17–21; Watson, S. & Arkinstall, S., The *G-Protein Linked Receptor Facts Book*, (1994), Academic Press). U.S. Pat. No. 5,223,409 discloses at columns 85 and 86 target materials or molecules, namely, "almost any molecule that is stable in aqueous solvent may be used as a target to which GPCR selectively responds.

With respect to volatile compounds that GPCRs react with, a great many are known which are foreign molecules which are evolutionarily 'unknown' to the organism until they are encountered for the first time (Getchell, T. V., Physiol. Rev. (1986) 66:772–787; Lancet, Ad D. Ann. Rev. Physiol. (1986) 9:329–37; Beer, H. In, *Handbook of Biosensors and Electronic Noses: Medicine, Food and the Environment* (1997) CRC Press, pp. 521–532; Alone, E., In, *Hanbook of Biosensors and Electronic Noses: Medicine, Food and the Environment* (1997) CRC Press, pp. 503–519; Zhao, H. et al. (1998) Science 279:237–242). Nevertheless, they are readily detected and discriminated. The inherent molecular specificity in recognizing and discriminating myriads of foreign compounds should be understood to be a characteristic of GPCRs which, using techniques well known in the art described above, are design-engineered into GPCRs for use in the sensing elements of the present invention.

Accordingly, the present invention provides apparatus and method particularly advantageous for on-site detecting or measurement of contamination by specific toxic materials. In Paddle, B. M., (1996)Biogen. Bioelectr. 11: 1079–1113, Tables 2, 3, 4, 5 at pp. 1084–1093 is presented by way of illustration rather than limitation toxic materials and pathogenic organisms that might be considered biological or chemical warfare agents which are subject to detection by the methods and apparatus of the present invention.

The constituents of explosive materials comprise ligands which are subject to detection by the methods and apparatus of the present invention. These explosive include but are not limited to trinitrotoluene (TNT), cyclonite (RDX), pentaerythritol tetranitrate (PETN) C-4 class explosives, and combinations thereof (Yinon, Y. and Zitrin, S. (1993) Modern Methods and Applications in Analysis of Explosives, John Wiley & Sons, Ltd., Sussex, U. K.)

The method and apparatus of the invention finds further use in detecting process stream ligands in the chemical and food industries, such as, but not limited by the examples in Kress-Rogers, E. (1997) Handbook of Biosensor and Electronic Noses Medicine, Food, and the Environment, CRC Press, Boca Raton, see Chptr 19, Table 19.1, 19.2, 19.3, 19.4, 19.7. Environmental contaminants which are detected by the apparatus and method of the invention are also disclosed in National Research Council Report entitled "Safe Water From Every Tap: Improving Water Service to Small Communities, Natl. Acad. Press, Washington, D. C. Other environmental contaminants of importance regulated by the U.S Environmental Protection Agency are disclosed at the website www.epa.gov/toxicants.

For quality assurance and quality control in the food industry, the methods and apparatus of the invention are used in process stream monitoring and other modes to measure chemical and microbial properties of products. These properties relate to measuring parameters of product quality, such as aroma and taste, nutritional value, functional properties, and compliance with specifications or regulations. Parameters involved in screening for product safety are measured, such as chemical contamination by residues, toxins and taints; microbial contamination, as measured by total load, pathogens, and indicators of their activity. Products stability parameters are measurable by the methods and apparatus of the invention, such as chemical reactions and microbial growth as seen in water activity, solute concentrations, pH value, and preservative concentration.

Sensing Element Comprising GPCR for Detecting A Ligand

In FIG. 4, the sensing element 12 of the invention includes GPCRs preferentially selective for a ligand of inter est. The GPCR is heterologously expressed in a transformed eucaryotic cell 14. Methods for providing a GPCR for use in the invention in eucaryotic cell types are described above.

Preferred cells for use in the invention are fungal cells, and most preferred are yeast cells (U.S. Pat. Nos. 5,691,188 and 5,482,835). Yeast cells which are particularly useful in the invention include, but are not limited to are Saccharomyces cerevisiae (Blumer, K. J. et al. (1991) ann. Rev. Physiol. 53:37–57; Price, L. A. et al. (1995) Molec. Cell Biol. 15:6188–6195; Sprague, G. F. Jr. (1991) TIG 7:393–398; Ne, D. et al. (1997) J. Biol. Chem. 272:15553–15561; Price, L. A. et al. (1996) Molec. Pharm. 50:829–837; Prasad, K. R. and Rosoff, P. M. (1992) Cell calcium 13:615–626; Bach, M. et al. (1996) Receptors and Channels 4:12914 139; Marsh, L. (1991) Ann. Rev. Cell Biol. 7:699–728; *Schizosaccharomyces pombe* (Arkinstall, S. et al. (1995) FEBS Let. 375:183–187; (Sander, P. et al. (1994) FEBS Let. 344:41–46; Ficca, A. G. et al. (1995) FEBS Let. 377:140–144;, and Pichia pastoris (Abdulaev, N. G. et al. (1997) Protein Expression and Purification 10:61–69;, and *Zygosaccharomyces rugxii* (Nishi, T. and Yagi, T. (1993) J. Gen. Appl. Micro. 39:493–503. Other fungal cell useful in the invention include but are not limited to *Aspergillus niger* and *Ustilago maydis* (Regenfelder, E. et al. (1997) EMBO J. 16:1934–1942.

The invention provides these cells in a form containing a calcium binding chromophore which fluoresces or increases its fluorescence in response to binding free cytoplasmic $Ca^{++}$ as a result of influx of calcium via an endogenous calcium channel which is coupled to the GPCR and activated by selective binding of the GPCR to a ligand of interest. Accordingly, there is a rapid and sensitive change in the cells' optical properties, e.g change in fluorescence of the chromophore, which provides a rapid means to visualize, and hence report by means of the apparatus of the invention the cells' selectivity to ligand binding and to define the sensitivity of a variant GPCR, i.e. a GPCR receptor specific binding affinity for a ligand of interest. In this way, any particular GPCR sequence can be mutated and screened in reasonable time for specific, preferential recognition of a very wide variety of target molecular species or ligands which are quite different in structure (i.e. shape and charge) from the natural receptor ligand. Furthermore, the reporting function, which involves changes in fluorescence features of the cells in selective response to a ligand of interest, used in the screening process also can be exploited in the detection mode of a biosensor using GPCRs heterologously expressed in eucaryotic cells, and preferentially yeast cells.

In synthetic membrane systems well known in the art (Schmid, E. et al. (1998) Anal. Chem. 70:1331–1338; Heyes, S., et al. (1997) Biochemistry 37:507–522; Schmid, E. et al., (1998) Biosensors 98 (Abst.) Elsevier Science Publ., ed. Turner, A. P. F. p. 158; Heyse, S. et al. (1998) Biosensors 98 (Abst.) Elsevier Science Publ., ed. Turner, A.P.F. p. 159; Sevin-Landais, A.-F. et al. (1998) Biosensors 98 (Abst.) Elsevier Science Publ., ed. Turner, A.P.F., p. 160; Stora, T. et al. (1998) Biosensors 98 (Abst.) Elsevier Science Publ., ed. Turner, A. P. F., p.161). GPCRs are oriented 78 and immobilized and stabilized 80 in functional form for purposes of making the sensing element 12 of the invention (Heyes, S., et al. (1997) Biochemistry 37:507–522). The sensing element 12 of the invention embodied in a synthetic membrane system permits GPCRs to detect ligands at attomolar concentrations ($10^{-18}$M) (Schmid, L. et al. (1998) Anal. Chem. 70:1331–1338). There is a rapid and sensitive change in the electrical characteristics of the synthetic membrane system 76 in response to the ligand binding by the GPCR 26 in the synthetic membrane (ligand binding coupled to ion channels leads to ion pumping, i.e., a change in charge density in the synthetic membrane in response to ligand binding by the GPCR). This change in electrical characteristic of the synthetic membrane is measured by a monitoring means 80 such as surface plasmon resonance (Kress-Rogers, E. (1997) Handbook of Biosensors, Chapter 7), or by patch clamp monitoring means 80 (Chandy, K. G. and Gutman, G. A. (1995) Ligand and Voltage Gated Ion Channels, CRC Press, Ann Arbor, Mich.; Hille, B. (1992) Ionic Channels of Excitable Membranes, Sinauer Assoc. Publs., Sunderland, Mass.) provides a rapid means to measure the synthetic membrane selectivity based on a GPCR receptor specific binding affinity for a ligand of interest.

In synthetic polymer systems well known in the art (U.S. Pat. Nos. 5,443,955; 5,571,401) (Cornell, B. A et al. (1997) Nature 387:580–583; ibid, Biosensors (1998) (Abstr.), Elsevier Science Ltd., ed. Turner, A. P. F.; Kress-Rogers, E. (1997) Handbook of Biosensor, Chapter 24, 25, 26; Chen, G. et al. Nature Biotech. (1997) 15:354–357; Mosbach, K. and O. Ramstrom, Biotechnology (1996) 14:163–169), in which, according to an aspect of the invention, a GPCR is placed, there is a rapid and sensitive change in the electrical characteristics of the synthetic polymer system 76 in response to the ligand binding by the GPCR in the synthetic polymer (ligand binding coupled to ion channels leads to proton pumping, i.e., a change in charge density in the polymer in response to ligand binding by the GPCR). This change in electrical characteristics of the synthetic polymer provides a rapid means to measure 80 the synthetic polymer's selectivity based on a GPCR receptor specific binding affinity for a ligand of interest.

In other cell types that possess GPCRs (e.g. mammalian fibroblasts, hepatocytes), there is a concomitant influx of $Ca^{++}$ via a calcium channel from the extracellular milieu into the cell upon GPCR-ligand binding. Therefore, the rapid (e.g., milliseconds) $Ca^{++}$ flux is exploited when coupled to a vital flourescent dye that binds free $Ca^{++}$ for optical detection of the rapid fluorescence response (Molecular Probes, Incorporated, Corvallis, Oreg.; Set 20: Calcium Indicators, Chelators, and Ionophores).

Accordingly, the sensing element of the present invention comprise a GPCR, the GPCR having specific binding affinity or being preferentially responsive to a specific substance, and reporting the detection of that substance through optical changes or through electrical characteristic changes in a cell hosting the GPCR. One of the preferred embodiments of the sensing element involves a transformed cell line expressing one or more different GPCRs or functional fragments thereof, the cell line preferably being a transformed eucaryotic cell line heterologously expressing one or more GPCRs, and more preferably a yeast cell line.

Biosensors

It should be understood that the apparatus 10 of the invention, as shown in FIG. 2, is a biosensor that comprises a biological sensing element 12, a GPCR, in intimate contact with, embedded in, or linked to a physical transducer (automatic optical detection means 20), whereby in combination they relate the detection of a target ligand 24 or specific substance 24 with some measurable signal. The sensing element 12 or sensor 12 provided by the present invention comprises a GPCR which recognizes the ligand. The transducing system translates the recognition or detection event into a signal which can be monitored, compared, and otherwise processed to provide desired information about the ligand of interest, including detection of substances, objects or people with which the ligand is associated.

Vapor-Phase Detection

As described below, the methods and apparatus of the present invention relate to detecting a ligand 24 using a sensing element 12 to determine the presence of a ligand in a gas or vapor, or to detect a ligand associated with an airborne particle, or ligand in association with airborne biological or chemical aerosol particles in a gaseous sample.

Dry air is chemically a gas mixture. Air contaminants, being a multiplicity of substances, change the composition of this gas sometimes considerably. In this context, ligands or chemical compounds have special significance either in solid form or sorptively bonded on or to coarse or fine dust particles. These dust particles are supplied to the normal air either by natural processes (for example, by vulcanizing action) or by the activity of people.

These so-called environmental chemicals can be roughly classified as gases and aerosols based on their physical characteristics. Of great significance are those environmental chemicals (that is, environmental noxious materials such as allergens, pesticides and the like) which occur to an increasing extent as a toxic-substance burden of outside and indoor air for persons and animals. Burdening of the air by coarse and fine dust can be especially seen in large cities and industrial areas. Dust having particles below 5 microns obtain access to the lungs, that is, they enter the alveoli. These particles can collect there or pass into the blood, penetrate into body cells and damage the metabolic enzymes, trigger allergies, and the like. If several environmental noxious materials appear simultaneously in the air, then synergistic effects are possible.

Aerosols are by definition two-phase systems in which solid or liquid particles/substances are finely dispersed in a gas phase; that is, in these two phase systems, air functions as a carrier and distribution medium for these particles/substances. If, for example, biological materials, such as spores, viruses or bacteria are dispersed in air, then this can be characterized as biological aerosols or bioaerosols. So called solid aerosols are those which contain solid substances in dispersion. The size distribution of particles contained in aerosols extends over a spectrum of particles having diameters of $10^{-3}$ microns up to approximately $10^2$ microns.

In order to exclude health dangers, for example at the workplace, specific limit values are defined in appropriate regulations. If the occurrence of dangerous substances (aerosols) cannot reliably be excluded in the air at the workplace, then the workplace has to be monitored with respect to a drop below the limit values (maximum workplace concentration, permitted concentration, biological workplace tolerance value). Such a monitoring can be performed using the methods and apparatus of the invention.

Liquid Phase Detection

As used herein, the term "liquid phase" means chemicals or particles either in solution in or suspended in a liquid phase that could include water or other solvents or liquid media. Liquids may carry many substances, some of which are in true solution while others are insoluble but exists in a colloidal state. The ligands or analytes of interest may then either be in solution or merely carried by the liquid phase to the sensing element.

Apparatus Embodiments

Referring to FIGS. 1 and 2, respectively, embodiments of the invention are directed to an apparatus 10 for detecting a ligand 24 in vapor phase or in liquid phase. The apparatus comprises a sensing element 12 which comprises a GPCR, means for exposing 22 a candidate substance to the sensing element, and means for monitoring 20 response of the sensing element 12.

Sensing Element (12). The GPCR of the sensing element is preferentially responsive to a ligand of interest in a candidate substance. As described above, methods for making GPCRs specific for one or more of a large scope of ligands of interest are well known in the art. See FIG. 6 which shows a GPCR 26 embedded in a cell membrane 27. Also available to those skilled in the art are well known techniques for constructing cells which express the GPCR(s) of interest.

Typical methods useful in the invention for making a sensing element are disclosed in U.S. Pat. Nos. 5,482,835 and 5,691,188. Transformed yeast cells heterologously expressing a GPCR of interest are made, in particular, cells in which the endogenous calcium channel are linked to the heterologously expressed GPCR in the appropriate genetic construct for non-promiscuous calcium signaling.

The transformed yeast cells are incubated in a $Ca^{++}$ binding fluorophore permeable to the transformed cell membrane. In operation, GPCR binding of a ligand of interest opens up a calcium channel, allowing an influx of free $Ca^{++}$ into the cell, which is rapidly bound by the fluorophore which immediately changes the fluororesence properties of the cell, hence reporting ligand of interest recognition. The change in the cells' optical properties, e.g. fluorescence, provides a means to define the preferential response and sensitivity of a variant GPCR for a ligand or specific substance of interest.

The sensing element 12 encompasses GPCRs expressed in other types of eucaryotic cells. Examples of known eucaryotic cell types whose GPCRs are well characterized and by standard genetic engineering methods are heterologously expressed in other eucaryotic systems include vertebrate cells, such as but not limited to mammalian fibroblasts, mouse and human neuroblastoma cells, Chinese hamster ovary cells, various human cancer cell line, oocytes. The yeast system is described in (U.S. Pat. Nos. 5,576,210 and 5,284,746) (King, K. et al., Science (1990), 250:121–123; Sizmann, D. et al. Receptors and Channels (1996), 4:197–203; Bach, M. et al. (1996) Receptors and Channels 4:129–139; Marsh, L. et al. (1991) Ann. Rev. Cell Biol. 7:699–728; Price, L. A. (1995) Molec. Cell Biol. 15:6188–6195. Other references of interest are McClintock, T. S. et al., Analyt. Biochem. (1993) 209:298–305; O'Dowd, B. F. et al., Genomics (1995), 28:84–91; Knapp, R. J. et al., FASEB J. (1995), 9:516–525; Weyer, U. et al. Receptors & Channels (1993), 1:193–200; In all cases the cloned and expressed GPCR most of which did not occur endogenously in the expression cell type functioned as determined either by ligand binding and/or the G-protein mediated cellular responses to the ligand. This ability of heterologous GPCR to be expressed in a broad range of eucaryotic cell types is based upon the high degree of sequence homology of their transmembrane regions and G-protein coupling regions 82, particularly the alpha subunit of the G-protein, for the different GPCRs (see for example Strosberg, A. D. Eur. J. Biochem. (1991); Strader, C. D., et al. Ann. Rev. Biochem. (1994) 63:101–132; Tesmer, J. J. R. et al., (1997) Gilmore, et al. (1997) Science 278:1907–1916). For example, the primary sequence identity of the transmembrane domain of receptors in species homologs of a given receptor is 85–95% and 60–80% of a related subtype receptor. (Strosberg, ibid).

Certain GPCR are coupled to $Ca^{++}$ channels in specific cells types, usually in me vertebrate cells and particularly excititory cells, and in yeast. For example, in fibroblast cells, when the GPCR is activated by its ligand, an associated $Ca^{++}$ channel is activated leading to a concomitant influx of $Ca^{++}$ This GPCR coupling activates Protein Kinase C (PKC) leading to the production inositol-1,4,5-triphosphate ($IP_3$), rather that activating adenylyl cyclase and generating cAMP. In yeast, the mating pheromone GPCR is coupled to calcium via an adenyl cyclase system (Marsh, L. et al. (1991) Ann. Rev. Cell Biol. 7:699–728). The flux of $Ca^{++}$ is rapid (msecs) and in the invention is coupled to $Ca^{++}$ fluorophores which are well known in the art thereby reporting the ligand binding event (Fishman, H. A. et al. PNAS USA (1995) 92:78777881; Molecular Probes, Incorporated, Corvallis, Oreg.; Set 20: Calcium Indicators, Chelators, and Ionophores).

As shown in FIGS. 1–3 and 5, the transformed cells useful in the invention are viably retained in the apparatus 10 in a cartridge 28 (FIG. 7) which is preferably demountable from the apparatus in a position so that the means for exposing 22 a candidate substance to the sensing element 12 brings vapor-phase specimen of the candidate substance to the sensing element 12.

A typical demountable cartridge 28, as shown in FIG. 7, has the following structure: A cartridge body 30, typically plastic, houses the cells and hydrogel 16. The cartridge 28 has an O-ring groove 34 with an O-ring to ensure that the cartridge 28 is sealed tight against extraneous vapor or liquid input. The cartridge will either snap or screw into the device, making the cartridge easily changeable. A protective, semi-permeable membrane 18 (e.g. Teflon™, methymethacrylate, cellulose acetate, Teflon™ polycarbonate or polydimethyl siloxane) is used to protect the immobilized cells 14 from erosion due to liquid flow or extreme dessication under vapor flow. (Reddy, S. M. & Vadgama, P. M. In, *Handbook of Biosensors and Electronic Noses: Medicine, Food, and the Environment* (Kress-Rogers, E. Ed.), pp.111–136). A light absorptive coating 32 is positioned on the side of the cells opposite the light source 36 to prevent source light 38 from reflecting back into the fluorescence detector 40, which receives a flourescent signal 39 from the sensing element 12. For liquid or vapor phase detection, a cartridge contains an optical window 42 adjoining the flow channel 22 opposite the position of the cells 14 and adjacent to the light source 36 and photodetector 40. Because the cartridge is replaceable, upon replacement a fresh, clean optical window 42 is provided which replaces an optical window 42, which due to prior use, may be optically deteriorated (e.g. fouled or otherwise altered by deposition of materials from vapor or liquid sampling).

A variety of flow chambers 22 are useful in the apparatus, however, a preferred flow chamber, illustrated in FIGS. 1–3, 5, 8 and 9 has the following structure: The GPCR-containing cells 14, supported by a hydrogel 16 which has been anchored to an optically-opaque, light absorptive stage 32, are disposed preferably but not necessarily as a monolayer which is protected from mechanical distress or excess dehydration by a semipermeable membrane 18 which allows exposure of the sensing element to the ligand 24 in the vapor phase or liquid which has been transported to the sensing element 12 by the exposing means 22.

The sensing element 12 is also in a position subject to scrutiny by monitoring means 20 for monitoring response of the sensing element. Accordingly, the viable cells 14 heterologously expressing GPCR, i.e. sensing element, are retained in a cartridge 28 adapted to receive a continuous or intermittent flow of air or liquid, as shown in FIGS. 1–3, 5, 8 and 9, containing the candidate substance in a flow chamber 22. One face 44 of the sensing element 12 in the cartridge 28 is exposed to the main stream flow in the flow chamber 22 and this face 44 contains the sensing element 12. In a preferred embodiment, the cells 14 may be retained in a cartridge 28 by means of a binding agent 16 that is biologically compatible with the cells and provides nutrition for the cells. A preferred class of binding agents is hydrogels. Examples of synthetic hydrogels include, but are not restricted to, polyvinyl chloride, polyethylene, poly(methyl) methacrylate, poly(2-hydroxyethyl) methacrylate, polyvinyl alcohol, and polyvinyl pyrrolidone, while several natural hydrogels may also be used (e.g., cellulose, alginates). (Thomson, R. C. et al. In, *Molecular Biology and Biotechnology: A Comprehensive Desk Reference* (1995), VCH Publishers, Inc.; Heichal-Segal, O., et al. Biotechnology (1995)13:798–800); Peppas, N. A. ed. *Hydrogels in Medicine and Pharmacy,* (1987), Vol. 2, Polymers. CRC Press; Bickerstaff, G. F. ed., (1997) Immobilization of Enzymes and Cells, Humana Press, Inc., Totowa, N.J.). Preferred hydrogels include the calcium alginates (Korpan, Y. I. et al. (1994) Biochemistry-Moscow 59:141–143; Sroka, W. and Rzedowski, W. (1991) Biotechnol. Let. 13:879–882).

Hydrogels provide a support for the attachment and growth (i.e. immobilization) of the cells. Formulated with nutritional media, hydrogels provide nutrition to cells as the hydrogel absorbs 30–90% by weight of biological fluids such as nutritional media. For example, yeast cells immobilized are in a hydrogel as a monolayer of cells to optimize cell exposure to the vapor containing the ligand of interest and optimizes detection of fluorescence changes by the monitoring means when the GPCR embedded in the host cells of the monolayer detect the ligand of interest.

Exposing means 22 typically include a flow chamber in which the cartridge 28 is mounted for intaking a vapor stream or a liquid stream containing a candidate substance (see FIGS. 1–3, 5, 8 and 9). To maintain suitable and constant flow rates over the sensing element 12, the flow rate can be controlled using a fan 46 (for vapor) or propeller (for liquid), or alternatively by a remote pump 48 directing a flow of liquid or vapor into a flow chamber 22 containing the sensing element 12 which may be housed in a demountable (replaceable) cartridge 28. In certain embodiments of the apparatus (FIG. 5), the flow chamber 22 containing the sensing element 12 is remotely disposed from the remainder of the apparatus, a wire 50 or wireless signal transmission functionally connecting the flow chamber to the remainder of the apparatus. The flow chamber is designed to generate laminar flow over the cartridge sensing element to maximize exposure of the sensing element to the candidate substance and minimize the unstirred boundary layer between the mainstream flow and the sensing surface 44.

Preferred design elements of a flow chamber 22 for a vapor-phase device involve an instrumental setup, as shown in FIGS. 1 in which the apparatus consists of means for exposing 22 a vapor-phase specimen of candidate substance to the sensing element 12. The exposing means is typically a tube with an entrance protected by a mechanical dust/particle filter 52 through which air comprising the vapor-phase specimen is collected, and enters the apparatus. A charcoal filter 54, in a preferable version, is placed over the air flow inlet 56 to obtain a base-line reading of the vapor. The exposing means 22 may comprise means for drawing a predetermined volume or amount of ambient atmosphere containing a vapor-phase specimen from a selected vicinity, for example, the vicinity of an individual or object passing through a customs station or area of restricted access. The exposing means may define an enclosed or partially enclosed chamber into which an individual or a part thereof may be disposed. For example, a compartment in which an individual's hand may be inserted may form a convenient exposing means. The exposing means may further include means for drawing air from the vicinity of the individual's hand into the apparatus. Light baffles 58, heat exchangers 60 or other temperature controlling devices may be situated in the exposing means 22 to limit exposure of the sensing element 12 to ambient light, large temperature fluctuations or extremes in temperature.

The specimen is directed by the exposing means 22 to the sensing element 12, which is disposed so as to be under the optical or electrical scrutiny of the monitoring means 20. Referring to FIGS. 1, 2, 3, 5, 8, and 9, the optical detection system 20 is basically a fluorometer. The light source 36 is preferably a high-intensity output blue light emitting diode (LED) with a fused lens tip which is adjacent to an optical band-pass filter 62 (interference filter). The LED is used as a light source 36 to excite fluorescence at a peak wavelength defined by the absorption maximum of the $Ca^{++}$ fluorophore. In a preferred embodiment, Calcium Green™ (Molecular Probes, Inc.) is the fluorophore with a peak excitation wavelength of 500 nm. The outputs and sensitivities of the light source LED and the photodiode detector are matched to the absorption maxima and emission maxima of the fluorophore of choice. Since the LED emits light over a broad range of wavelengths, short-pass cut-off filter is incorporated into the transmitter channel that effectively blocks all wavelengths longer than 510 nm. A long-pass cut-off filter is incorporated into the receiver channel so that no significant light is received at wavelengths shorter than 530 nm. Cut-off or interference filters useful in the invention include but are not restricted to Ratten™ interference filters and Corning™ filters. The fluorescence meter measures surface emitted light (fluorescence) (39) at a peak wavelength of 550 nm (the peak wavelength emission of Calcium Green™) that is excited by source light 38 at wavelengths shorter than 510 nm. The fluorometer employs a high-frequency, phase lock-loop synchronous detection system (for stray light rejection) which eliminates noise from ambient light. The LED is electronically modulated and a detector 40 will be phase-locked to the source modulation. The detection scheme effectively subtracts out any ambient light so that the resultant analog signal 64 is proportional only to the magnitude of the fluorescence 39. The fluorometer provides two analog outputs 64 via a bulkhead connector. One of the analog outputs provides a DC voltage proportional to the output of the fluorescence photodetector. The second analog output provides a DC voltage for the LED reference detector. The reference output is required to calibrate the fluorescence signal 39 relative to the excitation flux incident on the immobilized cells of the sensing element. Both analog outputs are in the range of 0–10 volts. The fluorescence meter requires an externally applied DC power 66 which is supplied via the same bulkhead connector that contains the analog output. The DC power can be derived either directly from batteries (in a portable or hand-held embodiment (FIG. 1) of the apparatus) or from an AC-DC power converter 66.

The photodetector 40 can be a monolithic photodiode with an on-chip amplifier having high responsivity, e.g. 0.45 amps/watt, and low noise ($NEP=10^{-14}$ $watts/Hz^{1/2}$, for example, Burr Brown OPT 101. However, other photodetector systems available in the art are suitable for the apparatus.

The transducer output 64 is a high level signal linearly related to the source lumination 38 and easily buffered for digitization. Commercially available interfaces are suitable for digitizing the signal and transferring the data via standard serial interface protocols to a local or remotely located microprocessor. A Martel™ Instant Interface is an example. Embedded in the microprocessor 68 are recognition and control routines known to those skilled in the art designed to activate appropriate utility actions 70 (e.g. alarms, LED, door lock solenoid, chart recorder) via general purpose I/O control lines.

The apparatus may further encompass means 68 for comparing the response of the sensing element with a previously established response for the ligand. A typical comparing means for use in the apparatus comprises a memory adapted to store a library of signals characteristic of ligands, objects and individuals associated with ligands, and including means for comparison of the signals from the sensing element with the signals contained in the library. The library is contained in a microprocessor 68 (e.g. Tattletale™ Microprocessor). Standard pattern recognition techniques or a neural network may be adapted to retain characteristic features of the signal profile for incorporation into the library.

It is understood that the flow chamber 22 contains a thermistor probe to monitor 72 close to the sensing element 12 the temperature of the incoming flow steam of vapor or liquid (depending on the aspect of the invention). The thermistor is electrically connected to a microprocessor 74 to allow for automatic correction of thermal effects ($Q_{10}$) on response time of the sensing element.

The source diode 38 and the photodetector 40 are controlled by electronics common to the art, and in a preferred version includes means for comparing 68 the response of the sensing element to a previously established responses for the ligand of interest. Typical comparing means include appropriate algorithms for signal variations and comparisons to standards as is well known to the art (Mendelson, Y. in *Biomedical Engineering Handbook,* J. D. Bronzino, ed. (1995) CRC Press, pp. 764–787).

In a preferred embodiment, the apparatus further comprises utilization means 70 responsive to the comparing means for providing an appropriate action. Examples of appropriate action include but are restricted to entry access, passage through a check point, access to information, credit or other data bases. Other appropriate actions include control over a transport device that carries an object through or into facility or apparatus. These actions are achieved by providing an annunciator as utilization means for alerting an operator to results of a comparison made by the comparing means. Other utilization means for use in the device are selected from the group consisting of, but not restricted to, a doorlock, or other automatic access-control device, a lock or other automatic access control device, and an automatic transport device.

In one embodiment of the liquid medium detection apparatus, utilization means responsive to the comparing means are provided for providing an appropriate action. Examples of appropriate action include but are not restricted to control of flow of liquid medium, such as in process stream monitoring. This action is achieved by providing an annunciator as utilization means for alerting an operator to results of a comparison made by the comparing means. Other utilization means for use in the device are selected from the group consisting of, but not restricted to, automatic valves, flow control devices, or other automatic access- or flow-control devices.

Apparatus for Detecting Specific Objects or People

Another aspect of the invention involves an apparatus for detecting specific objects or people. As described above for vapor phase detection, the apparatus comprises a sensing element that includes one or more GPCRs, means for exposing an object or person to the sensing element, and automatic monitoring means connected to receive a response from the GPCR.

In a preferred embodiment, the apparatus further comprises utilization means responsive to the comparing means for providing an appropriate action. Examples of appropriate action include but are restricted to entry access, passage through a check point, access to information, credit or other data bases. Other appropriate actions include control over a transport device that carries an object through or into facility or apparatus. These actions are achieved by providing an annunciator as utilization means for alerting an operator to results of a comparison made by the comparing means. Other utilization means for use in the device are selected from the group consisting of, but not restricted to, a doorlock, or other automatic access-control device, a lock or other automatic access control device, and an automatic transport device.

In operation, a typical use of the device is security access at airports, borders, or other public places. For example, at an airport, the apparatus is used to non-invasively detect (i.e. the apparatus does not directly or physically contact the object or person, persons or objects carrying illicit drugs (e.g., heroin, cocaine, marijuana, amphetamines) or explosives (TNT, RDX, PETN). Accordingly, the sensing element includes a GPCR specific for detecting an illicit drug or an explosive. The apparatus is positioned in the carry-on luggage metal detector monitoring system and/or in the metal detector through which passengers gain entry to secure airport areas. The means for exposing the sensing element draws an air flow across persons or objects into the flow chamber of the apparatus which exposes the sensing element to the ligands of interest to be detected. The GPCR binds the ligand which causes an optical change in the sensing element which is monitored and compared to established patterns of responses for the ligands of interest. When the ligand of interest is detected, an annunciator in the form of an alarm (e.g. acoustic, optical, or electrical) alerts the operator or other automatic utilization means to thereby control the person's or object's access to the secure space.

In use for drug interdiction or detection of chemical/biological warfare agents (i.e ligand or substance of interest), particularly in a covert detection mode, the apparatus is deployed remotely in a variety of scenarios, including a series of devices located at the perimeter of a defined zone of interrogation with each device operating in a stand-alone mode but capable of reporting independently or collectively through radio transmissions, or electromagnetic waves the localized detection of the ligand of interest. Such application finds use in law enforcement, national security, public safety operations. In yet another mode of use, the apparatus of the invention could be deployed remotely at check points, passageways, major transportation arteries, shipboard, cargo holds, storage areas, shipping/trucking/train ports for monitoring and detection of ligands and substances of interest. In a further mode of use, the apparatus could be deployed in an expendable manner from aircraft, ships, or trucks for wide-area and large scale surveillance and monitoring with a telemetric reporting capability coupled to a global positioning system to permit precise localization and detection coordinates.

Still another aspect of the apparatus for detecting a ligand comprises a sensing element which includes a GPCR, means for exposing a candidate substance to the sensing element, and means for monitoring response of the GPCR. It will be understood that the term "sensing element which includes a GPCR" is used to include (1) a single GPCR specific for a single ligand; (2) a plurality or array of different GPCRs specific for a plurality of specific ligands, respectively; (3) a plurality or array of different GPCRs specific for a single ligand (particularly for a large molecular species of a ligand). In the presence of an array of GPCRS, the apparatus comprises monitoring means which include means for comparing a pattern of responses from the array with a previously established pattern of responses for the specific substance. The monitoring means are selected from the group consisting of automatic optical means for detecting a change in optical characteristics of the sensing element, as described above, and automatic electronic means for detecting a change in electrical characteristics of the sensing element when the sensing element does not comprise a cell but instead comprises a at synthetic membrane or polymer system in which a GPCR is disposed, which is described in detail below.

In certain versions of the apparatus, the GPCR itself is labeled with a fluorescent chromophore. GPCR is chemically modified by covalently bonding a fluorescent chromophore, such as IANBD (N,N'-dimethyl-N (iodoacetyl)-N'-(7-nitrobenz-2-oxa-1,3-diazol-4yl) ethylene diamine (Gether, U. et al. Biochem. Soc. Trans. (1995) 23:96–102; ibid, J. Biol. Chem. (1995) 47:28268–28275). Ligand binding by GPCR is detected by techniques well known in the art for measuring protein conformational changes detecting fluorescence changes (e.g. fluorescence decay or lifetimes) upon binding of a ligand of interest by the GPCR. One skilled in the art can readily adapt the above-described optical system through light-source control and standard algorithms for detection of fluorescence lifetimes.

The apparatus further comprises means for comparing the response with a previously established response for the ligand. Utilization means responsive to the comparing means for providing an appropriate action are included in a further version of the apparatus. Utilization means are described above.

Substance Detection.

The apparatus and method of the invention are directed to detecting ligands in a medium. It will be appreciated that the apparatus and method are further directed to detecting substances. As discussed above, the terms "substance" and "ligand" are used to describe chemicals as follows: In some contexts, substance is used to refer to a candidate material which might or might not contain a ligand that the methods and apparatus of the invention are detecting. In other words, ligand is the chemical entity the methods or apparatus is looking for, and substance is the material in which the methods or apparatus are looking for it. In other contexts, substance is used for both the ligand or specific material that the methods and apparatus are looking for and the material in which it is being looked for (but the two are distinguished from one another by the term candidate appearing in the phrase "candidate substance"). In still other contexts, substance is used to refer to a material that the methods and apparatus are looking for, and that is known to contain a particular ligand—and the ligand is the target that the methods and apparatus use to seek and detect that sought-after material. Another definition of the term "ligand" as used herein is a molecule capable of being bound by the ligand-binding domain of a receptor, namely a GPCR. The molecule may be chemically synthesized or may occur in nature. Accordingly, the scope of the detailed descriptions contained for apparatus and methods directed to detection of ligands in a medium are co-extensive with the apparatus and methods directed to detection of substances in a medium.

Demountable Cartridge 28

In another preferred version of the invention (FIG. 9), an apparatus is provided for detecting a specific substance. The apparatus comprises multiple sensing elements in multiple demountable cartridges that include GPCRs which are preferentially responsive to the specific substance, means for exposing the sensing element to a candidate substance, means for monitoring the GPCR response. It is appreciated that the multiple, independent, demountable cartridge 28 for holding the sensing element 12 are used by an operator in selectively disposing the sensing element in position relative to the exposing means and the monitoring means for detection, or removing the sensing element from position for detection.

In a preferred version of this apparatus, the sensing element also includes a host structure which encompasses the GPCR and includes resources 16 for maintaining the host structure 14 with the GPCR. As described above, when the host structure comprises living cells, a hydrogel is used to immobilize the cells on the sensing element, the hydrogel further includes resources comprising nutrients for sustenance of the living cells. Another version of this apparatus involves a sensing element wherein the host structure is a synthetic membrane or a synthetic polymer system (see FIG. 10).

In another preferred version, the apparatus comprises a multiplicity or plurality of GPCRs of respective different types preferentially responsive to a corresponding multiplicity of respective different specific substances. In this version there is a corresponding multiplicity of cartridges as described, respectively holding different sensing elements, each comprising a different GPCR or different combination of GPCRS, said cartridges being substantially interchangeable. In this way, the apparatus is efficiently usable by an operator for detecting selectively any of the multiplicity of specific substances. It will be understood that the term sensing element which includes a GPCR" is used to include (1) a single GPCR specific for a single ligand; (2) a plurality or array of different GPCRs specific for a plurality of specific ligands, respectively; (3) a plurality or array of different GPCRs specific for a single ligand. In the presence of an array of GPCRs, apparatus comprises monitoring means which include means for comparing a pattern of responses from the array with a previously established pattern of responses for the specific substance.

A further preferred embodiment of the apparatus comprises means for holding a plurality of the cartridges, and means for automatically disposing cartridges of the held plurality at said detection position in turn, for detection of the corresponding specific substances in sequence. The means for holding a plurality of the cartridges is shown in FIG. 9, and is typically formed as multiple docking ports for the multiple cartridges. Means for automatically disposing cartridges are typically robotic arms, autonomous devices or remotely controlled devices or tethered devices which deliver the cartridges in position for detection of the specific substances.

Methods of the Invention

In broad scope, the invention provides a method for detecting a ligand in a medium. The method comprises the following steps. A sensing element is provided. The sensing element, as described above in detail, comprises a GPCR which is selectively responsive to a ligand of interest. The method involves obtaining a specimen of a candidate substance, which is either the ligand itself or contains one or more ligands of interest. In another step, the method exposes the sensing element to the specimen, and monitors the response of the sensing element. The method compares the response of the sensing element with a previously established response for the ligand(s) of interest. The method in one aspect is for a ligand in a vapor medium, and in another aspect is for detecting a ligand in a liquid medium. In either medium, the exposing step includes exposing the candidate substance to a sensing element which comprises one or more different GPCRs. The sensing element comprises one or more different GPCRs heterologously expressed in a eucaryotic cell line. A preferred sensing element comprises yeast cells which heterologously express one or more GPCR of various defined ligand specificities. The monitoring step preferably involves automatic optical detection of a change in optical characteristics of the sensing element. These steps and apparatus for carrying out these steps are described in detail above.

In a further aspect of the invention, the method involves the step of providing a GPCR that is preferentially responsive to a specific substance and the step of causing the GPCR to be exposed to a candidate substance, which comprises ligands of interest. These substances include chemical warfare agents, biological warfare agents, environmental contaminants or toxicants, heavy metals, other ions, process stream analytes, and clinically relevant ligands, the scope of these substances and ligands disclosed above. The step of causing includes at least one substep selected from the group consisting of incorporating the GPCR into a sensing element, shipping the new GPCR to a person for use in screening for the specific substance, and providing instructions for use of the new GPCR in screening for the specific substance or ligand.

A method of the invention is adapted for detecting specific objects or people. The steps, which are described in detail above, comprise the steps of exposing an object or person to a GPCR in a sensing element, monitoring response of the GPCR, and comparing the response with a previously established response for a specific object or person. A variation on this method involves an exposing step which includes exposing the object or person to an array of GPCRs having various different sensitivities, and the monitoring step includes comparing a pattern of responses from the array with a previously established pattern of responses for a specific object or person. In particular, the exposing step includes exposing the object or person to an array of transformed eucaryotic cells, preferably yeast cells, with GPCRs having various different sensitivities in the sensing element; and the monitoring step includes comparing a pattern of responses from the array with a previously established pattern of responses for a specific object or person, which have been described in detail above. Further versions of the monitoring step includes automatic optical detection of a change in optical characteristics of the sensing element, or the monitoring step includes automatic optical detection of a change in fluorescence or change in conformationally induced or amplified fluorescence of transformed eucaryotic cells in the sensing element, as described above.

In a variation of the method, a step is provided in which the GPCR that is preferentially responsive to the specific substance is disposed in a host structure which is selected from the group consisting of eucaryotic cells, synthetic membrane systems, and synthetic polymer systems. Examples of eucaryotic cells whose endogenous GPCRs have been heterologously expressed in yeast include mammalian fibroblasts, mouse and human neuroblastoma cells, Chinese hamster ovary cells, various human cancer cell line, oocytes, yeast algal and vascular plant cells.

Typical synthetic membrane systems 76 (FIG. 10) which find use in the invention are liposomes, other combinations of lipids, fatty acids and proteins that will form membrane-like vesicles. Typical synthetic polymer systems 76 include but are not restricted to conducting organic polymers derived from aromatic or heteroaromatic materials e. g. polypyrrole, methyl pyrrole, poly(5-carboyindole) (Persaud, K. C., and Travers, P. J., in *Handbook of Biosensors and Electronic Noses: Medicine, Food, and the Environment* (Kress Rogers, E. ed. pp. 563–592).

Detection Method that Involves Manufacturing Steps

In another aspect, the method for detecting a specific substance comprises the step of manufacturing a biosensor that includes living cells physically suspended on a hydrogel and drawing nourishment from material held within the hydrogel. This step is described in detail above. The method involves causing the cells to be exposed to a candidate substance, monitoring response of the cells to the candidate substance, and comparing the response with a previously established response for the specific substance.

In another method of detecting a specific substance, a step of manufacturing a biosensor which includes a GPCR is disclosed which requires incorporating into the GPCR a signaling element, which is selected from the group consisting of a chromophore for responding to a substance by fluorescing, a color change, and an electrical mechanism for responding to a substance by a change in an electrical property, as described in detail above.

The invention provides a method of making a biosensor for detecting a specific substance, which method is described above in detail. The steps of the method involve providing cells which are preferentially responsive to the specific substance, providing a hydrogel, providing nourishment, within the hydrogel, for the cells, physically suspending the cells on the hydrogel to draw nourishment from material held within the hydrogel, and incorporating the hydrogel, with the cells and nourishment, into a carrier or cartridge for exposure to a candidate substance. A further step involves functionally interconnecting (as described in detail above) the carrier with means for monitoring response of the GPCR to the candidate substance, as described below. The apparatus made by this method is also provided by the invention.

It is appreciated that the commercial applications of the apparatus and methods of the invention are widespread and include, without limitation, medical applications (e.g. analysis of body fluids for a range of components essential in modern medicine); biotechnology and chemical engineering (e.g. analytical monitoring of fermentation or process stream monitoring for pollutants, contaminants); food and drink industry (e.g. monitoring of pollutants, contaminants, and quality control of analyte concentrations); environmental monitoring (e.g. analyses of pollutants in water and air); defense and security industries (e.g. monitoring for chemical or biological warfare agents) (Eggins, B. (1997) Biosensors: An Introduction, John Wiley & Sons; Chapter 10)

Accordingly, the present invention is not limited to the specific embodiments as illustrated herein, but is only limited by the following claims.

What is claimed is:

1. Apparatus for detecting a ligand in a vapor medium; said apparatus comprising:
    (a) a sensing element which comprises at least one Guanyl-Nucleotide-Binding Protein Coupled Receptor (GPCR);
    (b) means for exposing a vapor medium to the sensing element;
    (c) automatic monitoring means for monitoring response of the sensing element; and
    (d) utilization means, responsive to the automatic monitoring means;
        wherein the utilization means are selected from the group consisting of:
            an annunciator for alerting an operator to results of the comparison,
            a door lock or other automatic access-control device for admitting or not admitting a person to a facility,
            a lock or other automatic access-control device for enabling or not enabling a person to have access to use of a facility, an apparatus, credit, information, or a service, and
            an automatic transport device for carrying or not carrying an object through or into a facility or apparatus.

2. The apparatus of claim 1, wherein:
    the sensing element includes one or more different GPCRs.

3. The apparatus of claim 1 wherein said sensing element comprises one or more different GPCRs expressed in a transformed eucaryotic cell line.

4. The apparatus of claim 1 wherein said sensing element further comprises a fluorescing element which produces said response upon binding of said ligand to said GPCR.

5. The apparatus of claim 4 wherein said fluorescing element is a calcium binding chromophore.

6. The apparatus of claim 3 wherein the eucaryotic cell line is selected from the group consisting of vertebrate cells, invertebrate cells, plant cells, algal cells, and fungal cells with the proviso that the eucaryotic cell line cannot be a frog melanophore.

7. The apparatus of claim 6 wherein the eucaryotic cell line is a yeast cell line.

8. The apparatus of claim 6 wherein the yeast cell line is selected from at least one of the group of cell lines consisting of *Saccharomyces cerevisiae, Schizosaccharomyces pombe,* and *Pichia pastoris,* and *Zygosaccharomyces rugxii.*

9. The apparatus of claim 6 wherein said fungal cells are selected from at least one of the group consisting of *Aspergillus niger* and *Ustilago maydis.*

10. The apparatus of claim 1, wherein:
the monitoring means comprise optical means for detecting, substantially in real time, a change in optical characteristics of the sensing element.

11. The apparatus of claim 1 wherein the exposing means include means for directing a vapor-phase specimen of the candidate substance to the sensing element.

12. The apparatus of claim 1 further comprising means for comparing the response with a previously established response for the ligand.

13. Apparatus for detecting a ligand in a medium, said apparatus comprising:
(a) a sensing element which comprises at least one, GPCR expressed in fungal transformed eukaryotic cells;
(b) means for exposing a candidate medium to the sensing element;
(c) means for monitoring response of the sensing element; and
(d) utilization means, responsive to the automatic monitoring means;
wherein the utilization means are selected from the group consisting of:
an annunciator for alerting an operator to results of the comparison,
a door lock or other automatic access-control device for admitting or not admitting a person to a facility,
a lock or other automatic access-control device for enabling or not enabling a person to have access to use of a facility, an apparatus, credit, information, or a service, and
an automatic transport device for carrying or not carrying an object through or into a facility or apparatus.

14. The apparatus of claim 13 wherein the sensing element includes one or more different GPCRS.

15. The apparatus of claim 13 wherein said sensing element comprises one or more different GPCRs expressed in a transformed eucaryotic cell line.

16. The apparatus of claim 13 wherein said sensing element further comprises a fluorescing element which produces said response upon binding of said ligand to said GPCR.

17. The apparatus of claim 16 wherein said fluorescing element is a calcium binding chromophore.

18. The apparatus of claim 13, wherein:
said fungal cells are *Aspergillus niger* or *Ustilago maydis.*

19. The apparatus of claim 13, wherein:
the monitoring means comprise optical means for detecting, substantially in real time, a change in optical characteristics of the sensing element.

20. The apparatus of claim 13, further comprising means for directing a vapor-phase specimen of the candidate substance to the sensing element.

21. The apparatus of claim 13 further comprising means for comparing the response with a previously established response for the ligand.

22. The apparatus of claim 13, wherein:
the medium is liquid.

23. The apparatus of claim 13, wherein:
the medium is vapor.

24. Apparatus for detecting a specific substance; said apparatus comprising:
a GPCR that is preferentially responsive to a specific substance;
means for exposing a candidate substance to the GPCR; and
means for monitoring the response of the GPCR to the candidate substance; and
utilization means, responsive to the automatic monitoring means;
wherein the utilization means are selected from the group consisting of:
an annunciator for alerting an operator to results of the comparison,
a door lock or other automatic access-control device for admitting or not admitting a person to a facility,
a lock or other automatic access-control device for enabling or not enabling a person to have access to use of a facility, an apparatus, credit, information, or a service, and
an automatic transport device for carrying or not carrying an object through or into a facility or apparatus.

25. Apparatus of claim 24, wherein:
said specific substance consists of chemical warfare agents, biological warfare agents, toxic agents, narcotics, pharmaceuticals, explosives, process stream analytes, impurities, waste materials, or environmental pollutants.

26. The apparatus of claim 24, further comprising:
a sensing element in which said GPCR is incorporated.

27. The sensing element of claim 26, further comprising:
a fluorescing element which produces said response upon binding of said candidate substance to said GPCR.

28. The apparatus of claim 27 wherein said fluorescing element is a calcium binding chromophore.

29. The apparatus of claim 24, wherein said GPCR comprises one or more different GPCRs expressed in a transformed eucaryotic cell line.

30. The apparatus claim 29 wherein the eucaryotic cell line is selected from the group consisting of vertebrate cells, invertebrate cells, plant cells, algal cells, and fungal cells with the proviso that the eucaryotic cell line cannot be a frog melanophore.

31. The apparatus of claims 30, wherein said fungal cells consists of *Aspergillus niger* or *Ustilago maydis.*

32. The apparatus of claim 30 wherein the eucaryotic cell line is a yeast cell line.

33. The apparatus of claim 32, wherein:
the yeast cell line consists of *Saccharomyces cerevisiae, Schizosaccharomyces pombe, Pichia pastoris* or *Zygosaccharomyces rugxii.*

34. The apparatus of claim 24, wherein:

the monitoring means include means for detection, substantially in real time, of a change in optical or electrical characteristics of the sensing element.

35. Apparatus for detecting a specific substance, said apparatus comprising:

a sensor that includes:
- (a) a hydrogel containing nourishment for living cells, and
- (b) transformed eukaryotic cells heterologously expressing GPCR which is preferentially responsive to a specific substance, said cells disposed on the hydrogel to draw nourishment from within the hydrogel;

means, responsive to a characteristic of said cells for deriving a signal related to presence or absence of the specific substance; and means for exposing a candidate substance to the sensor.

36. The apparatus of claim 35 wherein the signal-deriving means comprise means for monitoring the response of the GPCR to the candidate substance.

37. The apparatus of claim 36, wherein:

the monitoring means include means for automatic detection of a change in optical or electrical characteristics of the cells.

38. The apparatus of claim 35, in further combination with
- (a) automatic means for comparing the change in characteristics with a change in the same characteristics in presence of the specific substance;
- (b) utilization means, responsive to the automatic comparing means; wherein the utilization means are selected from the group consisting of:
  - an annunciator for alerting an operator to results of automatic comparison,
  - a door lock or other automatic access-control device for admitting or not admitting a person to a facility,
  - a lock or other automatic access-control device for enabling or not enabling a person to have access to use of a facility, an apparatus, credit, information, or a service, and
  - an automatic transport device for carrying or not carrying an object through or into a facility or apparatus.

* * * * *